US012788880B2

(12) United States Patent
Blanco et al.

(10) Patent No.: US 12,788,880 B2
(45) Date of Patent: Nov. 10, 2026

(54) SYSTEMS AND METHODS FOR DETECTING DISRUPTIONS IN FLUID DELIVERY DEVICES

(71) Applicant: DEKA Products Limited Partnership, Manchester, NH (US)

(72) Inventors: Luis E. Blanco, Seattle, WA (US); John H. Wilcox, Rockledge, FL (US); John Clark Gray, Tallahassee, FL (US)

(73) Assignee: DEKA Products Limited Partnership, Manchester, NH (US)

( * ) Notice: Subject to any disclaimer, the term of this patent is extended or adjusted under 35 U.S.C. 154(b) by 545 days.

(21) Appl. No.: 18/212,596

(22) Filed: Jun. 21, 2023

(65) Prior Publication Data

US 2023/0347046 A1 Nov. 2, 2023

Related U.S. Application Data

(63) Continuation-in-part of application No. 17/985,638, filed on Nov. 11, 2022, which is a continuation of
(Continued)

(51) Int. Cl.
*A61M 5/168* (2006.01)
*A61M 5/172* (2006.01)
*A61M 5/50* (2006.01)

(52) U.S. Cl.
CPC ........ *A61M 5/16859* (2013.01); *A61M 5/172* (2013.01); *A61M 5/5086* (2013.01);
(Continued)

(58) Field of Classification Search
CPC .... A61M 2005/16863; A61M 2205/15; A61M 5/16859; A61M 5/172; A61M 5/5086;
(Continued)

(56) References Cited

U.S. PATENT DOCUMENTS 4,077,405 A 3/1978 Haerten et al.
5,984,894 A 11/1999 Poulsen et al.
(Continued)

FOREIGN PATENT DOCUMENTS

CA 2921304 A1 2/2011
JP 2004229680 A 8/2004
(Continued)

OTHER PUBLICATIONS

International Search Report and Written Opinion for corresponding patent application No. PCT/US2023/025882, dated Oct. 6, 2023, 14 pages.
(Continued)

*Primary Examiner* — Jason E Flick
(74) *Attorney, Agent, or Firm* — Reid Knott Cunningham

(57) ABSTRACT

A system and method are provided for monitoring characteristics of a fluid being delivered from a fluid medication delivery device to an infusion site associated with a user. Model creation and development comprises, for each of one or more associated fluid delivery operations, collecting data streams from various sensors, assigning a fluid delivery state to the fluid delivery operation, and determining fluid delivery characteristics based on waveforms representing the time series data streams, and generating retrievable models correlating determined fluid delivery characteristics with the assigned fluid delivery state. Model implementation includes collecting time series data streams corresponding to a current fluid delivery operation, identifying models based on a selected fluid delivery state and determined fluid delivery characteristics from the data streams, and determining a correction factor to account for a difference between observed and predicted fluid delivery values. Alerts and/or automated control are further provided based on the correction factor.

20 Claims, 24 Drawing Sheets

Related U.S. Application Data application No. 16/382,995, filed on Apr. 12, 2019, now Pat. No. 11,504,471.

(60) Provisional application No. 63/357,885, filed on Jul. 1, 2022, provisional application No. 62/656,646, filed on Apr. 12, 2018.

(52) U.S. Cl.
CPC ............. *A61M 2005/16863* (2013.01); *A61M 2205/15* (2013.01)

(58) Field of Classification Search
CPC ...... A61M 2005/2474; A61M 2205/18; A61M 2205/3553; A61M 2205/3569; A61M 2205/581; A61M 2205/582; A61M 5/14244; A61M 5/14248; A61M 5/168; A61M 5/16831; A61M 5/16854; A61M 5/142; A61M 5/24; A61M 5/2455; A61M 5/2466; A61M 5/16836; A61M 5/1723; A61M 2005/1726
See application file for complete search history.

(56) References Cited

U.S. PATENT DOCUMENTS

| | | | | |
|---|---|---|---|---|
| 6,362,591 | B1 | 3/2002 | Moberg | |
| 6,523,414 | B1 | 2/2003 | Malmstrom et al. | |
| 6,752,785 | B2 | 6/2004 | Van Antwerp et al. | |
| 7,621,893 | B2 | 11/2009 | Moberg et al. | |
| 7,654,127 | B2 | 2/2010 | Krulevitch et al. | |
| 7,892,199 | B2 * | 2/2011 | Mhatre | A61M 5/14566 604/65 |
| 8,287,516 | B2 | 10/2012 | Kommerup et al. | |
| 8,346,399 | B2 | 1/2013 | Blomquist | |
| 8,417,545 | B2 | 4/2013 | Galasso et al. | |
| 8,449,523 | B2 | 5/2013 | Brukalo et al. | |
| 8,486,020 | B2 | 7/2013 | Hills et al. | |
| 8,734,428 | B2 | 5/2014 | Blomquist | |
| 8,752,436 | B2 | 6/2014 | Beck et al. | |
| 9,968,742 | B2 | 5/2018 | Van Antwerp et al. | |
| 10,201,656 | B2 | 2/2019 | Rosinko | |
| 10,610,643 | B2 * | 4/2020 | Mazlish | A61M 5/172 |
| 2007/0083153 | A1 | 4/2007 | Haar | |
| 2007/0093753 | A1 | 4/2007 | Krulevitch et al. | |
| 2009/0069743 | A1 | 3/2009 | Krishnamoorthy et al. | |
| 2011/0224523 | A1 | 9/2011 | Budiman | |
| 2016/0310663 | A1 | 10/2016 | Dantsker | |
| 2016/0361491 | A1 | 12/2016 | Shaked et al. | |
| 2017/0181894 | A1 | 6/2017 | Marshall et al. | |
| 2018/0071450 | A1 | 3/2018 | Ruhland | |
| 2020/0121860 | A1 * | 4/2020 | Uber, III | A61M 5/16827 |

FOREIGN PATENT DOCUMENTS

| | | | |
|---|---|---|---|
| JP | 2016535607 | A | 11/2016 |
| WO | 2009109344 | A1 | 9/2009 |
| WO | 2010059588 | A1 | 5/2010 |

OTHER PUBLICATIONS 1-6; Mossman, May 17, John; 2010 "Insulin Pumps: Design Basics and Tradeoffs"; EE Times, Power Management Designline; pp. 1-6, May 17, 2010.

* cited by examiner

SYSTEMS AND METHODS FOR DETECTING DISRUPTIONS IN FLUID DELIVERY DEVICES

CROSS-REFERENCES TO RELATED APPLICATIONS

This application claims the benefit of, and priority to, U.S. Provisional Patent Application Ser. No. 63/357,885, filed Jul. 1, 2022, and is a continuation-in-part of U.S. patent application Ser. No. 17/985,638, filed Nov. 11, 2022, which is a continuation of U.S. patent application Ser. No. 16/382,995 filed Apr. 12, 2019, which claims the benefit of, and priority to, U.S. Provisional Patent Application Ser. No. 62/656,646, filed Apr. 12, 2018, the entirety of each of which are incorporated by reference herein and commonly owned.

This invention was made with government support under R43DK130036 awarded by National Institutes of Health, National Institute of Diabetes and Digestive and Kidney Diseases. The government has certain rights in the invention.

FIELD OF THE INVENTION

The present invention generally relates to systems and methods for measuring characteristics of a fluid flow, and in particular, for detecting infusion abnormalities.

BACKGROUND

Infusion pumps may be powered electrically or mechanically. Different pumps operate in different ways. In a syringe pump, fluid is held in the reservoir of a syringe, and a moveable piston controls fluid delivery. In an elastomeric pump, fluid is held in a stretchable balloon reservoir, and pressure from the elastic walls of the balloon drives fluid delivery. In a peristaltic pump, a set of rollers pinches down on a length of flexible tubing, pushing fluid forward. In an electrokinetic pump, an electrokinetic engine delivers electric potentials across an electrokinetic porous media, causing the electrokinetic solution with the engine to displace a movable partition initiating fluid delivery.

Insulin pump injections are administered to counteract a buildup of glucose in the blood after food ingestion and are thus administered many times in a single day through a cannula that is replaced at least every two to three days. Conversely, dual-hormone infusion pumps exist where medication is given to raise glucose levels and lower them through a combination of medicaments such as glucagon and insulin. Eventually, however, repeated needle/cannula insertions and chronic insulin exposure compromise the small patches of skin to which patients attach their pumps and infusion sets. This inevitably results in adverse outcomes for the insulin device, giving rise to various malfunctions.

As of 2023, an estimated one million people with diabetes globally use a combination of specialized insulin pumps to manage their blood glucose levels. However, many type 1 diabetic patients have reported malfunctions with their pumps and infusion sets, such as improper needle/cannula insertion into the skin, the development of kinks in the infusion cannula, blockages within the cannula, medicine leakage from the injection/infusion site, and/or issues with injections sites such as lipohypertrophy, scar tissue, infection, bleeding, bruising, pain, adhesive problems, and irritation. These malfunctions can severely hinder or completely halt the life-saving function of the device and lead to hazardous consequences to those living with this disease.

Therefore, it will be advantageous to provide a system to detect malfunctions within an infusion pump system and notify users and/or third parties of these malfunctions.

BRIEF SUMMARY

Many advantages will be determined and are attained by various embodiments as disclosed herein, which may for example include an apparatus and methods for detecting one or more malfunctions related to an infusion pump (e.g., insulin pump).

A sensor system is provided that actively monitors a pump's performance and fluid delivery to detect one or more changing conditions at the infusion site that indicate partial or total delivery failure of the fluid. One or more indicators may be provided for generating an audio, visual, text and/or email notification. The sensor may be incorporated into an adjunct device, such as a sensor housing as herein described, which connects to a conventional and/or new pump or may be integrated as part of a new pump and/or infusion set design. The sensor may provide diagnostic capabilities for the pump, the infusion site, and infusion set and provide user alerts about failed injections/infusions, decreasing pump performance, degradation of an infusion site, infusion set failures, and may predict delivery failure based on any detected abnormalities related to historic performance of the pump, infusion set and infusion site. This technology may improve safety and performance of the pump system and decrease or eliminate waste caused by failed injections/infusions (e.g., extra insulin or replacement pumps or infusion sets).

Various embodiments disclosed herein may determine when an injection/infusion site malfunction is occurring in real time during, but not limited to, insulin deliveries using an insulin pump. These malfunctions can be defined as, but are not limited to: leakages; blockages; kinking of the cannula that impedes medication flow; dislodgement of the cannula from the injection site; overall dislodgement of the infusion set from the body. The "smart" infusion set also distinguishes between healthy and unhealthy tissue that is being infused with medication using an algorithm that considers a patient's previous and current datasets gathered from an in-line sensor.

Embodiments of systems and methods disclosed herein may include and/or utilize an operational algorithm that obtains raw data from onboard sensors, parses data to retrieve specific features, and calculates specific time series related constants related to underlying actions of the system (e.g., tau, maximum pressure, etc.).

In one aspect, the algorithm may use values to approximate the most appropriate model, and calculate an error term that captures the difference between the raw data and the predicted model. In a related aspect, the calculated error term may be compared to historical error, wherein model parameters may be adjusted and optionally bounded (e.g., within a range) to minimize that error.

In another aspect, wherein for example the error is within an acceptable range, and there is accordingly no need to update the terms, if the error is outside the established bounds the terms can be updated and saved in memory for future comparisons.

In another aspect, the error may be regionalized wherein the magnitude of the error may be used for insight regarding system performance, both as a mechanical safety (e.g., is the dosing specific to the pump consistent, having similar performance compared to another pump, etc.) and as a global indicator (e.g., have environmental conditions changed that affect the machinery, has the injection medium changed, has fluid delivery been compromised, etc.).

In another aspect, for a system with safety redundancies, the algorithm may prioritize specific raw data values before considering secondary variables, or it may use a redundant sensor as a confirmation for the primary data stream via a weighted average.

In another aspect, the system may consider meta-data/meta-patterns to identify system integrity: for raw sensor data this may mean looking at changes in sampling intervals, changes in performance by comparing performance indicators saved to memory; in the instances of insulin pumps it may use bolus/basal change points to identify urgency of the user or degradation of the system.

In another aspect, the system may use sensor data (force, pressure, flow, volume, impedance, etc.) and apply machine learning and control system theory to assess pump medication delivery performance. This may allow the pump to recognize when fluid is built up in the line or the host is not receiving medication due to a leak, and controllably adjust the flow rate to compensate for the obstruction and/or sound an alarm to replace the infusion site.

In another aspect, the system may determine how much medication is going into the body and thereby assess total medication delivered to patient, total medication left in the system reservoir, total medication loss due to setup/workflow procedures, etc., and communicate that to other systems or use it to estimate impact. This knowledge may for example be used to auto-order new medication if the system is running out, or to better track consumption habits or worsening conditions of the patient in the event that it is an inpatient infusion pump. In the case of insulin pump systems, this knowledge of medication delivered may for example be used to estimate a new insulin on board metric, and using user specific values such as insulin to carb ratio or insulin sensitivity it can predict the impact the insulin will have on the patient, e.g., future blood glucose levels.

In another aspect, the system could also serve as a foundation to estimate blood glucose in the event of a CGM failure, based on an accurate representation of how much medication has gone in, any log of carbohydrate intake, and known physical activity changes in the user (sleep, exercise, stress, etc.).

In another aspect, the system can utilize accelerometer data and biometrics to identify user state such as activity and sleep, but it can also work to identify patterns not common to "normal" activity highlighting possible meta states such as stress or illness. This data can be confirmed using a smart device as an input, or the user can confirm the prediction of the system via a confirmation message in which the user replies "yes" or "no" to a prompt such as "are you sick?".

In another aspect, the system may update dosing regimens for users or insulin specific parameters such as insulin sensitivity or insulin to carb ratio by accurately assessing how much insulin is needed to reduce blood glucose after a carbohydrate intake.

In another aspect, for example wherein a blood glucose meter requiring a finger stick is utilized in the absence of a CGM, the system may utilize different sensor data from the pump and smart devices to estimate a continuous blood glucose which can be updated via new measurements from the blood glucose meter.

In another aspect, the system may be integrated into existing hardware including but not limited to an insulin pump, syringe pump, infusion pump, and the like. If so integrated, the onboard controller and associated algorithm may for example use the values it has stored in memory and/or as they are obtained. The system may also exist outside the physical hardware and for example can be on a separate smart device, computer, or cloud-based system to which the device is linked and can send data.

In another aspect, processing capabilities associated with the system may include or be executed from a separate computer which has a screen to report metrics such as but not limited to, total fluid delivered, fluid uptake by patient, fluid in the line, predicted BG, environmental impact on performance, performance rating, or patient condition based on fluid intake. If the system is hosted on the cloud, the hardware may connect to it wirelessly or via a direct electrical connection which communicates to the cloud.

In another aspect, the system may also be used as a bio safety mechanism which for example requires the user to intake a specified amount of medication for ensuring proper motor skills, such as before unlocking a smart device, operating heavy machinery or a car, opening a door, traveling, etc. For example, the system can detect how much medication has entered the body and send a wireless communication signal to a device which unlocks a device, or is activated specifically for that user.

In another aspect, the described technology can be adapted to other types of infusion pumps such as those used in chemotherapy, antibiotics, pain relievers, and other medications. The system could detect irregularities in drug delivery, including rate changes, leaks, or blockages, in these other types of pumps using the same principles outlined for insulin pumps.

In another aspect, the system may incorporate non-invasive monitoring technologies such as optical sensors, acoustic sensors, or RF sensors to monitor for changes in tissue health and infusion effectiveness. This could provide an alternative method for detecting site failures, leakages, or other issues without requiring additional hardware to be attached to the body.

In one aspect, the system employs machine learning algorithms to enhance its predictive and diagnostic capabilities. These algorithms could be trained on large datasets encompassing various infusion site failures, enabling the system to identify subtle patterns and correlations that may not be apparent to human observers. Over time, the system can refine its understanding and detection of failures through a process of continual learning and adaptation.

In another aspect, the system could incorporate additional data streams from wearable devices such as smartwatches, fitness trackers, and sleep monitors to further enhance its understanding of the patient's state. This could involve tracking physical activity, heart rate, sleep patterns, and other biometric data to identify changes that may impact insulin absorption or demand.

In another aspect, the system could leverage cloud-based analytics to process and analyze data from multiple patients. This could allow healthcare providers to remotely monitor the performance of infusion pumps across a large patient population and to intervene proactively when issues are detected. In a telemedicine application, the system could send alerts to healthcare providers as well as patients, facilitating timely interventions and adjustments to treatment plans.

In another aspect, the system may incorporate environmental sensors or data streams, such as weather data, to adjust its algorithms for detecting infusion failures. For instance, the system might adjust its expectations for insulin absorption rates based on the ambient temperature or humidity, allowing it to detect failures more accurately under a range of environmental conditions.

BRIEF DESCRIPTION OF THE SEVERAL VIEWS OF THE DRAWINGS

For a better understanding of the technology, reference is made to the following description, taken in conjunction with any accompanying drawings.

DETAILED DESCRIPTION

Figure 1A:
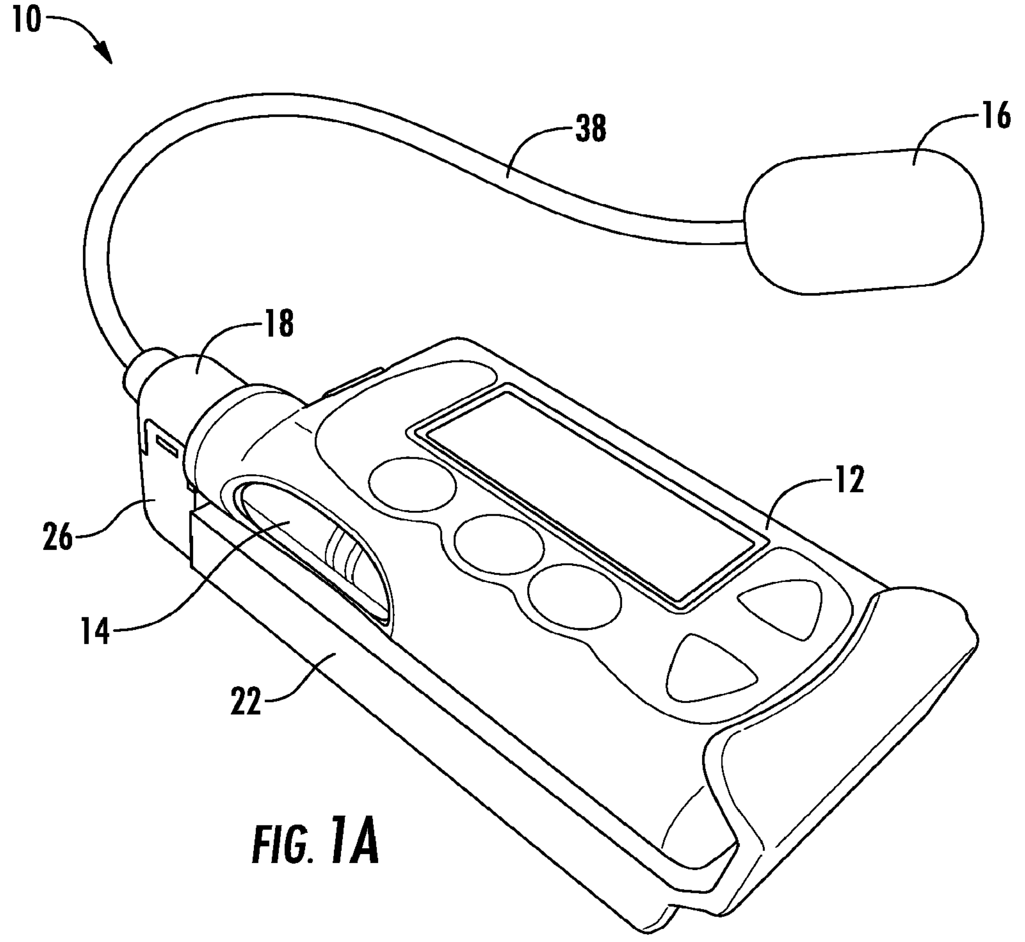
FIG. 1A depicts an exemplary system in accordance with the teachings of the present disclosure.

Systems and methods of the present disclosure will now be described more fully hereinafter with reference to the accompanying drawings, but should not be construed as limited to the embodiments set forth herein. Rather, these embodiments are provided so that this disclosure will be thorough and complete, and will fully convey the scope of the invention to those skilled in the art.

One or more embodiments of the present disclosure provide a sensor that actively monitors a pump's performance and fluid delivery in order to detect changing conditions at the infusion site that indicate insulin delivery failure.

With reference initially to FIGS. 1A-3, one or more embodiments of the present disclosure comprise systems and methods for monitoring characteristics of a fluid being delivered to a subject and/or detecting abnormalities and/or malfunctions within a fluid delivery system (such as an insulin pump or other device), within an infusion set, and/or at an infusion site of a subject. An embodiment of the system 10 may comprise (i) a pump 12 configured for delivering a fluid (such as, for example, insulin or other medicament or fluid); (ii) an infusion set 16 in fluid communication with the pump and configured for infusing a subject with the fluid; (iii) a sensor housing 18 providing a sensor 20 selectively coupled between the infusion pump 12 and the infusion set 16; and (iv) an electronics kit 22 configured for powering the sensor via an electrical connection 24 there between and analyzing and/or transmitting data collected from the sensor 20. Alternatively, the sensor 20 and/or sensor housing 18 may be incorporated entirely within a pump design (not shown) without departing from the spirit and scope of the present disclosure. Likewise, the electronics configured for receiving, storing, and/or analyzing data from the sensor may be housed within the pump itself. In some embodiments, the sensor and/or the associated electronics may be utilized to perform diagnostics on the injection site in order to monitor the performance of the infusion set, assess the health of the tissue, evaluate the viability of the infusion site, detect failed injections, detect infusion set malfunctions, monitor pump performance, and predict delivery failure based on any abnormalities detected by the system related to historic performance of the pump, infusion set, and infusion site.

In some embodiments, the pump 12 may comprise an infusion pump such as an insulin pump, but other suitable pumps are within the scope of the present disclosure. Moreover, one of skill in the art will appreciate that the sensor systems and methods disclosed herein may also be used in connection with other types of fluid delivery devices, e.g., a handheld syringe, intravenous fluid delivery systems, implantable delivery systems, medication delivery patches with microneedles, ambulatory pumps, stationary pumps, or medication injection pens without departing from the spirit and scope of the disclosure.

In some embodiments, the sensor 20 is configured for at least one of collecting and transmitting data pertaining to the fluid pressure. The data may be transmitted to and received by a secondary device, such as the electronics kit or other secondary device configured for receiving the data. Once a failure or malfunction is detected, an alert may be activated which indicates to the user and/or some third party that a problem exists. The alert may be an audio, visual, tactile, and/or message response (e.g., text and/or email) that originates from any suitable component of the system, including but not limited to the sensor, the pump, the sensor housing, the electronics kit, the infusion set, or other device. The sensor 20 may be electrically connected, either directly or by way of the electronics kit, to a Wi-Fi, radiofrequency, and/or Bluetooth™ transceiver and/or to other wireless type systems for communicating with a remote device such as a phone, watch, tablet, or computer to provide the alert.

Alternatively, the alert may be provided by at least one of the sensor and the electronics kit.

With continued reference to FIGS. 1A-3, some embodiments of the system 10 comprise a sensor housing 18 coupled on a first end to an infusion pump 12 and on a second end to an infusion set 16 configured for delivering fluid to a subject (such as a patient or a user). The electronics for measuring and analyzing changes in pressure detected by the sensor may be confined within an electronics housing, or kit 22, coupled to the sensor within the sensor housing via an electrical connection 24. The electrical connection may incorporate any type of connector (e.g., gold, silver, etc.) which connects the sensor housing with the electronics kit. Alternatively, the sensor housing 18 and/or the pump or infusion set may have all necessary electronics needed to measure and analyze changes in pressure or other fluid characteristics detected by the sensor.

In one or more embodiments, the electronics kit 22 may be sized and shaped to cradle the infusion pump for ease of use and handling. To protect the electrical connection from disruption, a wire housing 26 may be provided, which removably connects to the sensor housing by way of a suitable connector portion 28.

As depicted in FIGS. 4-10, some embodiments of the systems and methods disclosed herein comprise a sensor housing 18 having a first, or upper, connector portion 30 configured for connecting the sensor housing to the infusion set and a second, or lower, connector portion 32 configured for connecting the sensor housing 18 to the pump 12. An interior portion of the sensor housing provides a sampling chamber 34, or cavity, in fluid communication with the first and second connector portions 30, 32, which defines the location within the sensor housing 18 where characteristics of the fluid passing therethrough are measured and/or analyzed by the sensor 20. Alternatively, the sampling cavity may protrude from, or reside exterior to, a body portion of a sensor housing without departing from the scope of the present disclosure. In exemplary embodiments disclosed herein, a sensor chamber 36 is accessible from the exterior of the sensor housing 18, thereby enabling convenient placement and/or maintenance of the sensor 20 for measuring a fluid pressure or other fluid characteristic in said sampling cavity 34.

Figure 1B:
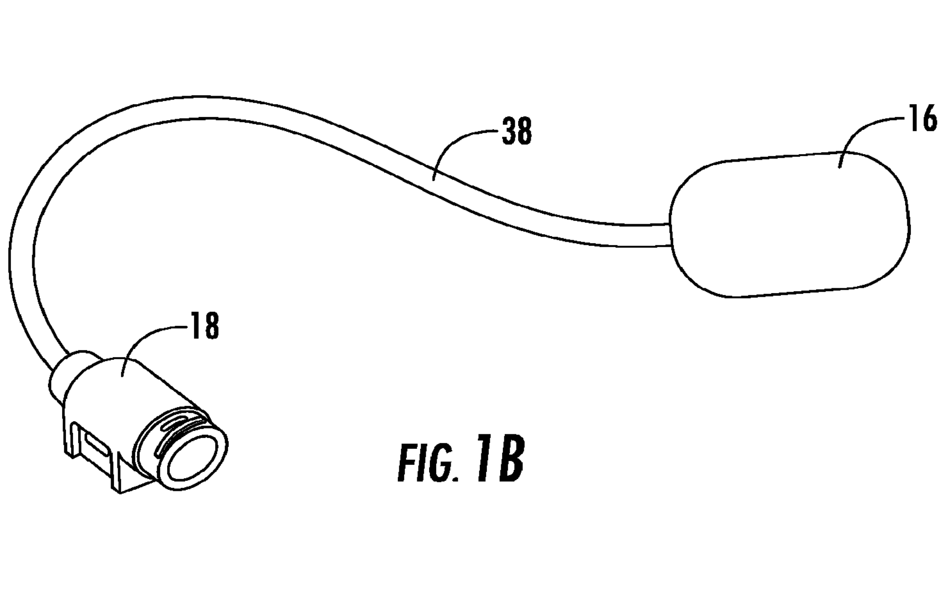
FIG. 1B depicts an exemplary "smart" infusion set in accordance with the teachings of the present disclosure.
Figure 2:
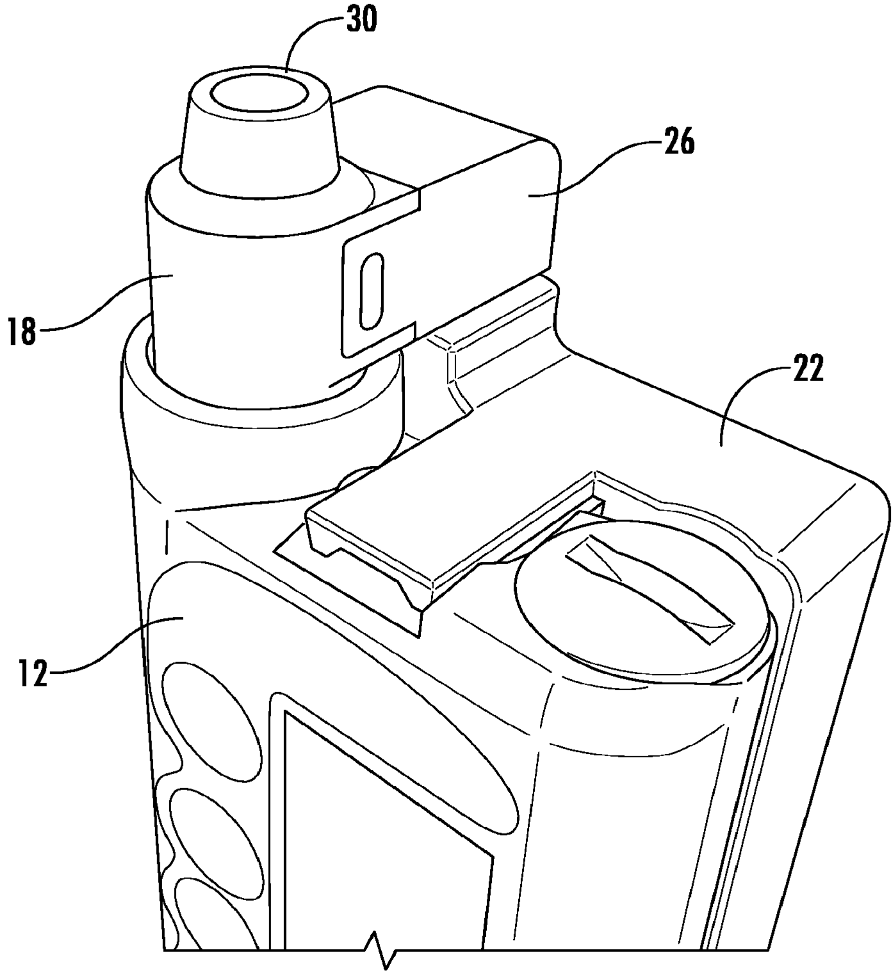
FIG. 2 depicts an exemplary system in accordance with the teachings of the present disclosure.
Figure 3:
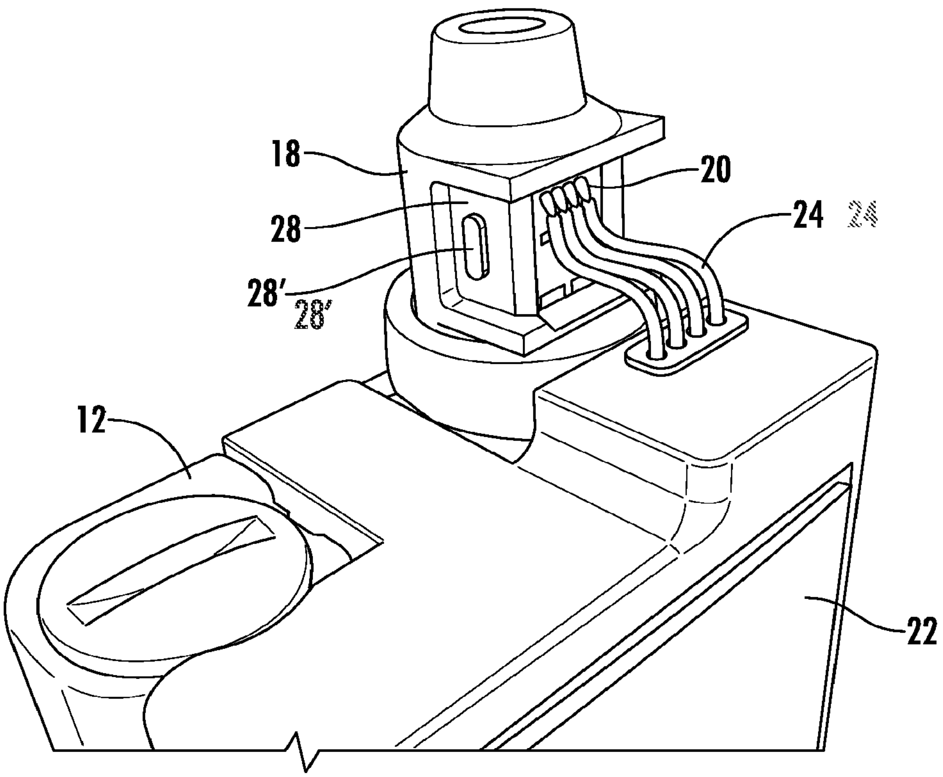
FIG. 3 depicts an exemplary system in accordance with the teachings of the present disclosure.
Figure 4:
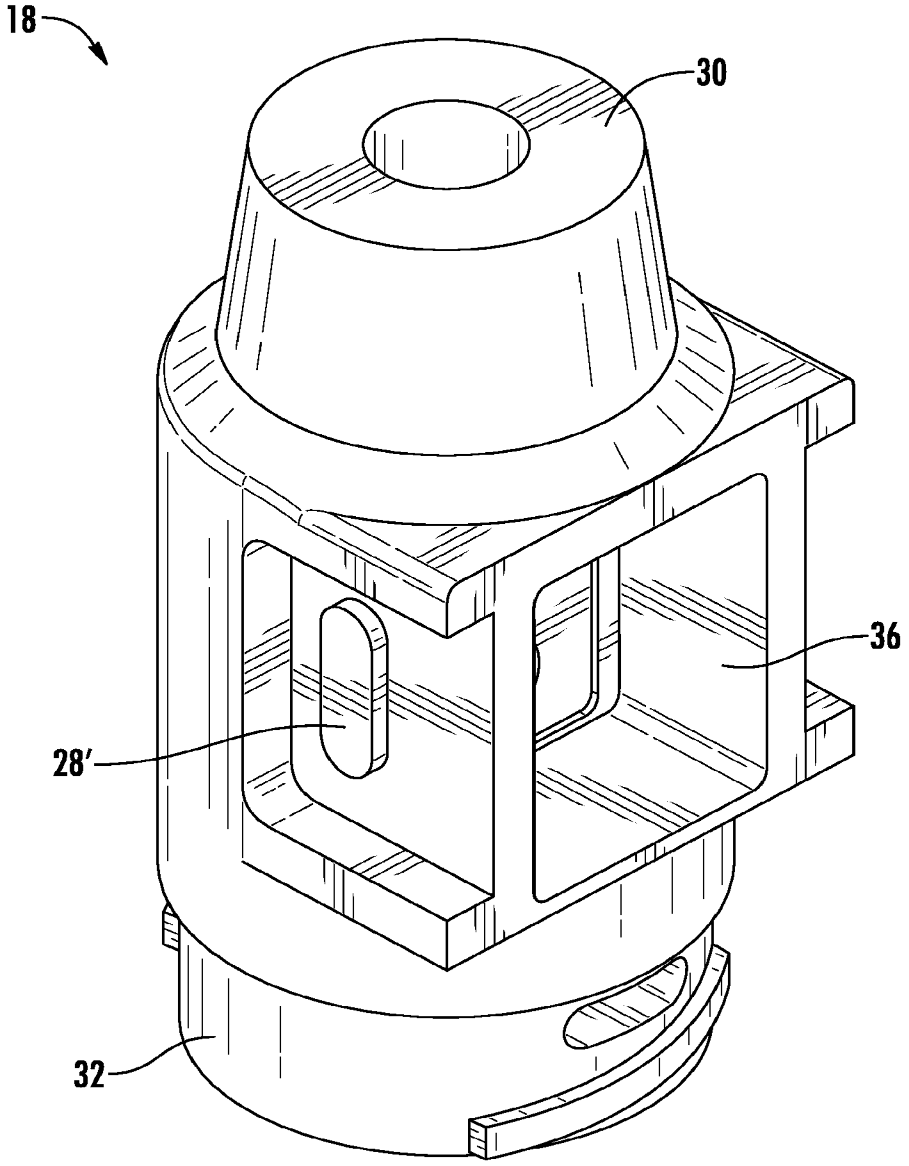
FIGS. 4-13 depict various views of an exemplary sensor housing.
Figure 6:
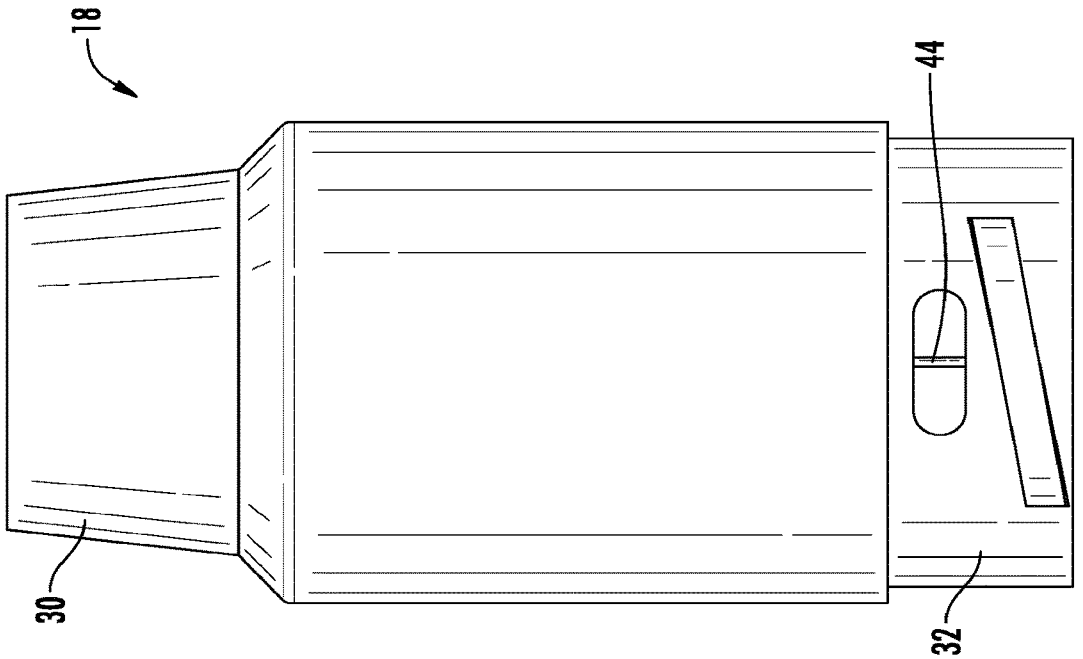

The first connector portion 30 may be connected to a tube 38 associated with an infusion set 16 to provide the fluid to the subject (see, e.g., FIG. 1). Tubeless embodiments, however, are envisioned. The tube 38 may connect to the first connector portion 30 using any suitable connecting means including, but not limited to, a threaded connection, a luer-type connection, a magnetic connection, and/or an adhesive, such as a suitable gluing composition or other permanent or semi-permanent connection. In an alternative embodiment, such as the embodiment of FIG. 1B, the sensor housing 18 may be an integral component of a unitary infusion set, wherein the tubing 38 is permanently affixed to the first connector portion 30 on one end and the patient interface of the infusion set 16 on the other end. In some embodiments, the tubing 38 is formed from polyurethane medical tubing, but other suitable materials, including but not limited to plastics, hypoallergenic materials, and chemically stable materials, are within the scope of the present disclosure.

Likewise, the second connector portion 32 may be connected to the pump 12 using any suitable connecting means, including but not limited to a threaded connection, a luer-type connection, a magnetic connection, and an adhesive, such as a suitable gluing composition, so long as the second connector portion 32 is placed in fluid communication with the fluid reservoir 14 within the pump 12 to permit the flow of fluid through the sensor housing 18. As will be apparent to one of skill in the art, any means of connecting the first and second connector portions to the infusion set and pump, respectively, should be water and air-tight to enable accurate measurements by an incorporated sensor.

Figure 12:
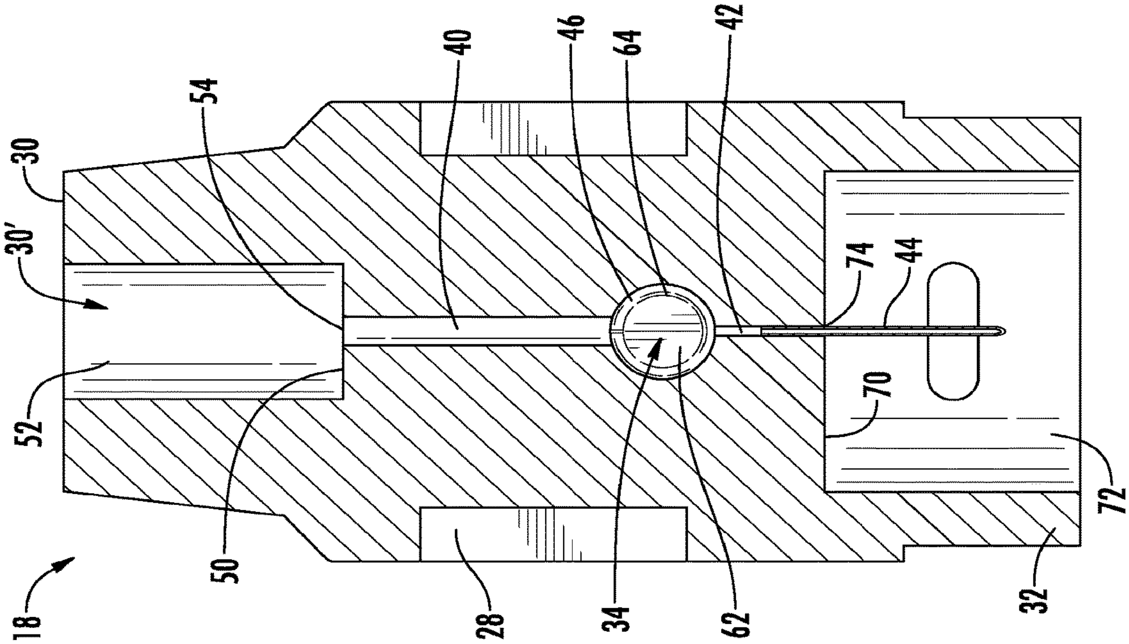
Figure 11:
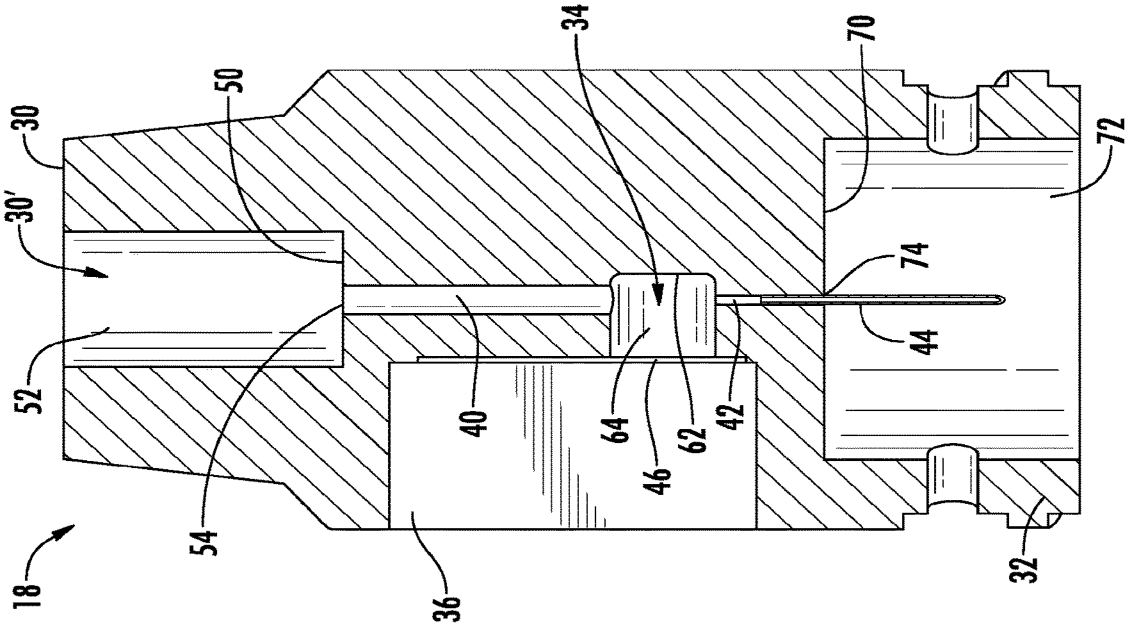
Figure 13:
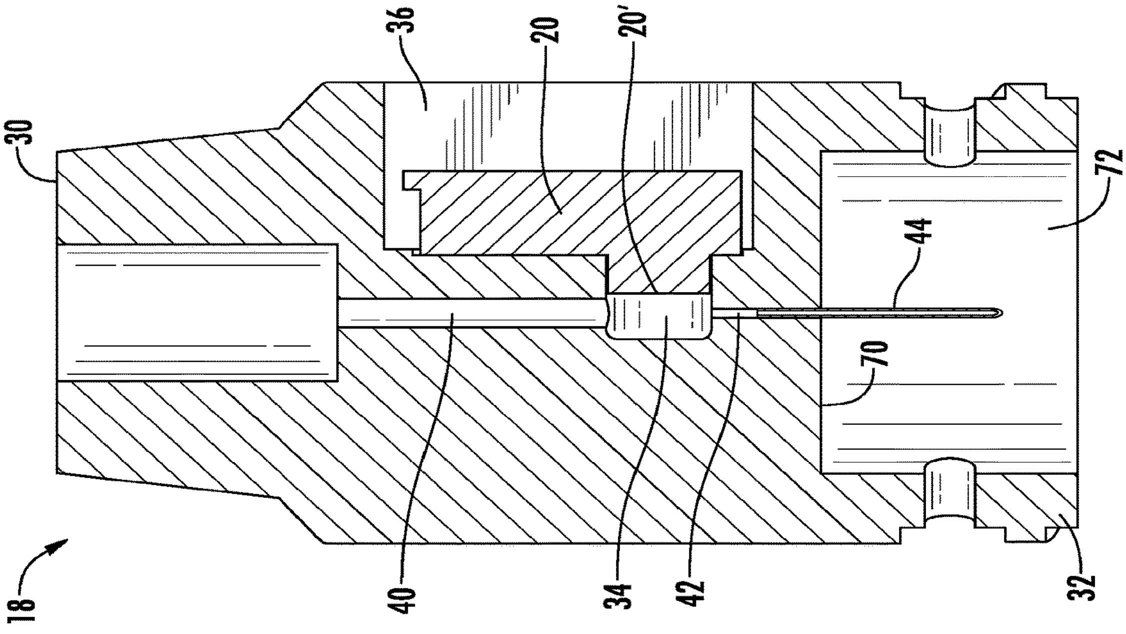

Referring now to FIGS. 11-13, which depict cross-sectional views of the exemplary sensor housing 18 of FIGS. 1A-10, embodiments of the systems and methods disclosed herein may comprise a sensor housing 18 having a first connector portion 30 configured to connect the sensor housing 18 to the infusion set 16 and a second connector portion 32 configured to connect the sensor housing 18 to the pump 12. A sampling cavity 34 may be positioned in-line between the first connector portion 30 and the second connector portion 32. In an embodiment, the sampling cavity 34 is in fluid communication with the first 30, or upper, and second 32, or lower connector portions via first 40 and second 42 channels, respectively. Embodiments devoid of first and second channels, however, are within the scope of the present disclosure. The first 40 and second 42 channels may provide a path for first and second needles 44, respectively. However, embodiments having only one needle 44 positioned within at least one of the first 40 and second 42 channels, as well as embodiments devoid of any needles, are within the scope of the present disclosure. As described above, a sensor chamber 36 in fluid communication with the sampling cavity 34 may also be provided, wherein the sensor chamber 36 may be configured for accommodating the sensor 20 for measuring a fluid pressure or other fluid characteristic in the sampling cavity 34. One or more embodiments may employ a medical pressure sensor, such as a NovaSensor NPC-120 sensor, that has pressure detecting capabilities relative to the pressures within the insulin or other pump. Other sensors, however, are within the scope of the present disclosure, such as, but not limited to, a piezoelectric sensor, or a sensor configured to detect at least one of voltage, current, electrochemical variations, optical, ultrasonic, or any other desirable characteristic.

In one or more embodiments, a needle 44 positioned within, adjacent to, and/or in fluid communication with the second, or lower, channel 42 pierces a fluid reservoir 42 of an insulin or other pump to enable a flow of fluid through the sensor housing 18. Stand-alone fluid reservoirs apart from a pump may also be utilized and engaged by the sensor housing. In one or more embodiments, the sensor housing 18 may be screwed onto the pump 12 with a twist and lock movement such that it is compatible with conventional insulin pumps that utilize tubing. In one or more embodiments, this twist and lock movement drives the needle 44 present in the lower portion of the sensor housing into a reservoir 14 of the pump 12, enabling the flow of fluid through the needle 44. This configuration may allow medication or other fluid to flow to the sensor 20 for detection of pressure or other changes or characteristics in the fluid. The sensor 20 may be located anywhere between the pump's medication reservoir and the tubing. In other embodiments, the sensor may be located anywhere between the pump and user. Medication or other fluid may flow through the sensor and pressure or other characteristics may be detected by, for example, an NPC-120 pressure monitor that is within the fluid pathway of the sensor.

In one or more embodiments, data collected by the sensor 20 during insulin pump medication deliveries may be monitored and/or analyzed by the sensor and/or the electronics kit, and any abnormal signals may result in an alert sequence. By registering pressures that are abnormal when compared to normal medication delivery sequences, the sensor can detect a malfunction associated with either the pump, infusion set or infusion site, as well as insulin pump blockages or leakages at the infusion site. Once the user is notified about a malfunction, they may be prompted to observe their infusion site and reinject their infusion kit into a new location. In one or more embodiments, the system may identify a suitable reinjection site for the user based on, for example, data in the system pertaining to prior fluid deliveries or the user's physiological response to the fluid delivery (e.g., increase or decrease in blood glucose).

One or more embodiments of the sensor housing 18 have a first connector portion 30 configured to connect the sensor housing 18 to an infusion set and a second connector portion 32 configured to connect the sensor housing 18 to a pump 12. A sampling cavity 34 may be positioned between the first connector portion 30 and the second connector portion 32, wherein the sampling cavity 34 is in fluid communication with the first and second connector portions via first 40 and second 42 channels, respectively. As described above, however, embodiments devoid of first and second channels are envisioned. In one or more exemplary embodiments, the first 40 and second 42 channels are configured to provide a path for first and second needles 44, respectively. In other embodiments, only one of the first and second channels are configured for receiving a needle 44. Embodiments devoid of needles are also envisioned. The sensor housing 18 may further comprise a sensor chamber 36 in fluid communication with the sampling cavity 34, the sensor chamber 36 configured for accommodating a sensor 20, wherein the sensor 20 measures a characteristic or property of the fluid in the sampling cavity 34.

In one or more embodiments, the sensor chamber 36 extends orthogonally to a flow path of fluid through the first 40 and second 42 channels. However, orientations other than orthogonal are envisioned, including orientations greater than or less than ninety degrees. In one or more embodiments, the sensor chamber 36 houses the body of an incorporated sensor 20, and enables a sensing portion 20' of a sensor 20 to engage fluid in the sampling cavity 34 through an aperture 46 formed in a portion of the sampling cavity 34. Embodiments devoid of a sensor chamber are also within the scope of the present disclosure. For instance, the body portion of a sensor 20 may be located remote from a sensing portion 20'.

In one or more embodiments, a tube 38, or other fluid channel, is connected to the first connector portion 30 on one end and an infusion set 16 on the other end, thereby enabling the delivery of a fluid to a subject. Tubeless embodiments are also envisioned.

The sensor 20 may be configured for at least one of collecting and transmitting data pertaining to the fluid, including but not limited to, fluid pressure, flow rate, viscosity, composition, pH, temperature, conductivity, impedance, fluorescence, absorbance, and/or the presence of absence of said fluid in the sampling cavity 34.

Figure 5:
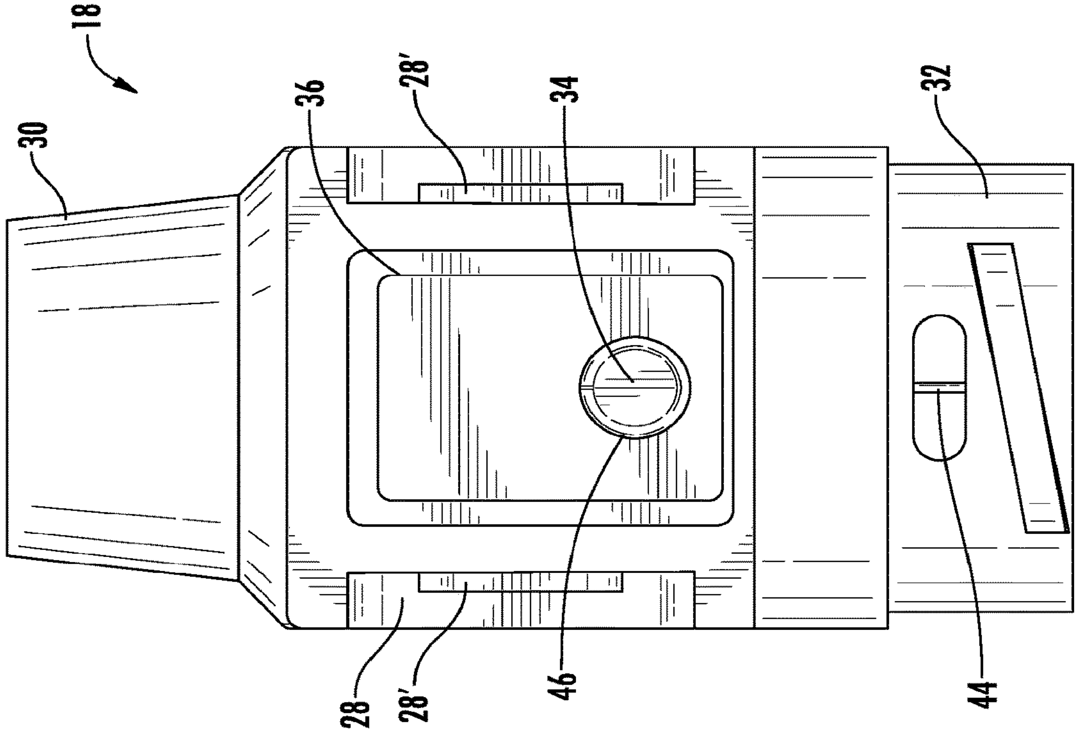
Figure 8:
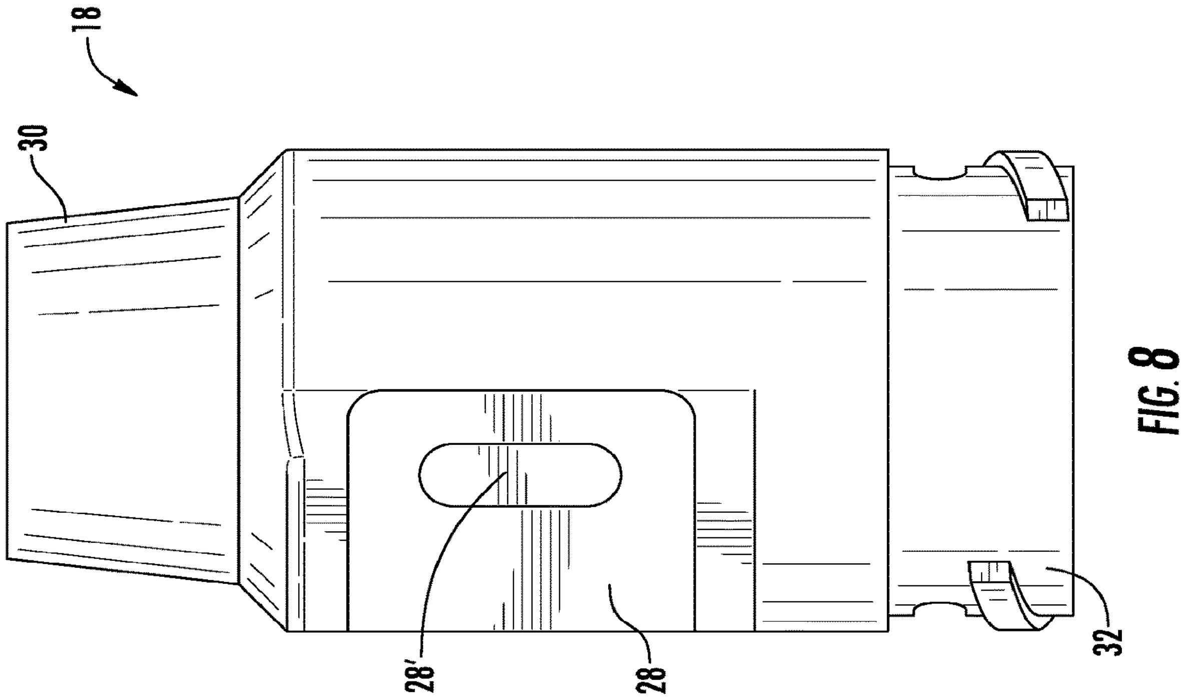
Figure 7:
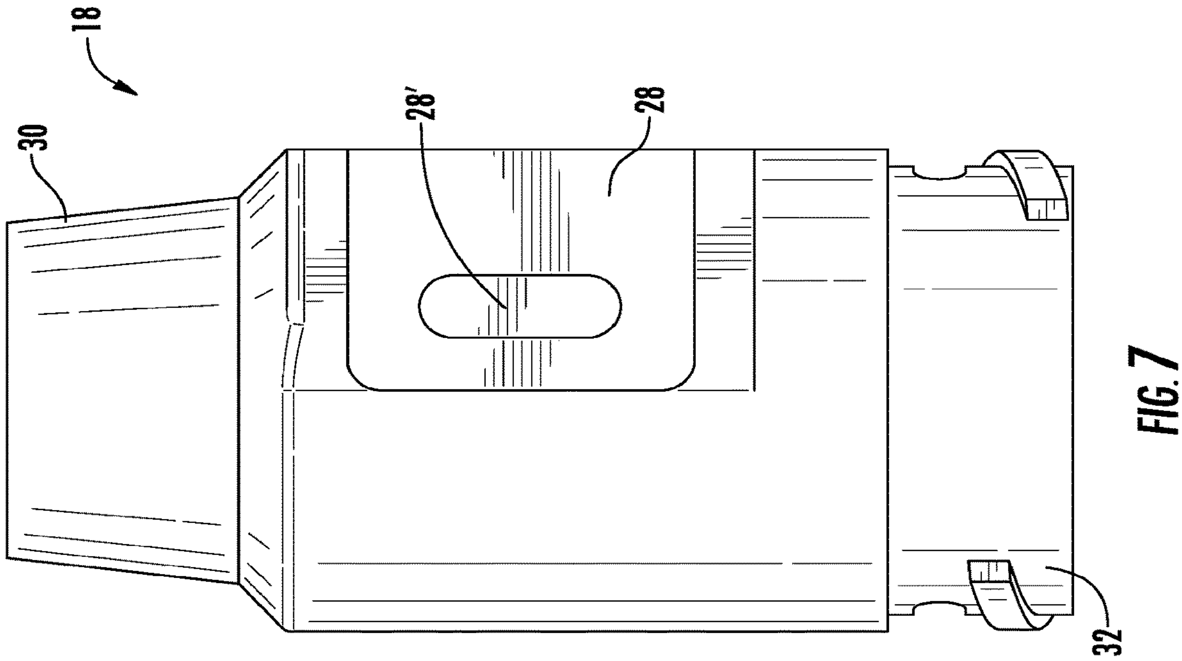
Figure 9:
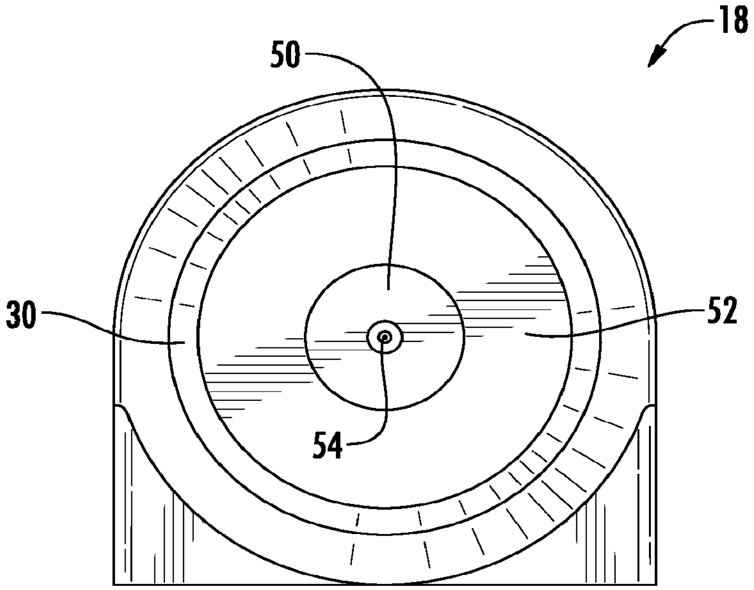
Figure 10:
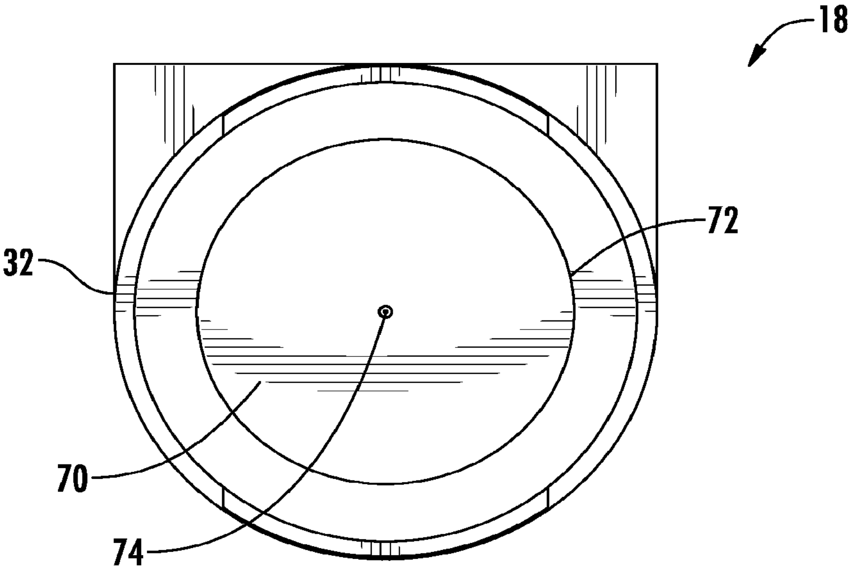

In one or more embodiments, a portion of the sampling cavity 34 is defined by a portion of the sensor 20, such as a sensing portion 20' of the sensor 20. Thus, a boundary of the sampling cavity 34 may be defined, in part, by a portion of the sensor 20 upon placement of the sensor 20 into the sensor housing 18. In one or more embodiments, the interface between the sensor 20 and the sensor housing 18 may comprise a membrane or other resilient seal for ensuring the connection, or interface, between the sensor 20 and the sensor housing 18 is water and air-tight to enable an accurate measurement of characteristics and/or properties of the fluid in the sampling cavity 34. As depicted in FIG. 5, e.g., the sampling cavity 34 may define an aperture 46 configured for receiving a portion of the sensor 20. The aperture may be circular, square, triangular, hexagonal, oval, or any other suitable shape.

As depicted in FIGS. 9-13, one or more exemplary embodiments of the sensor housing comprise a tapered first end 30 defining a first receiver 30' configured to receive an infusion set tube 38, wherein the first receiver 30' defines a substantially planar base portion 50 and a cylindrical sidewall 52 upstanding therefrom, the base portion 50 defining a first, or upper, aperture 54. Alternatively, the first end may not be tapered and/or the sidewall may comprise a shape other than cylindrical without departing from the scope of the present disclosure. As described above, the tube 38 may be removably connected to the first receiver 30' via any suitable connecting means, or may alternatively be permanently affixed to or integral with the first, or upper, end 30 to form a unitary infusion set comprising a patient interface, a sensor housing, and a tube or other fluid delivery means affixed therebetween as depicted in FIG. 1B.

As depicted in FIGS. 11-13, one or more embodiments comprise first 40, or upper, and second 42, or lower, internal channels in fluid communication with the first receiver 30 via the first, or upper, aperture 54. Each internal channel may have a uniform diameter along its length. Alternatively, the internal channels may have non-uniform diameters. In one or more embodiments, the diameter of the first internal channel 40 is greater than the diameter of the second internal channel 42. Alternatively, the diameter of the first internal channel 40 may be less than or equal to the diameter of the second internal channel 42. The first and second channels may be linear or nonlinear. In one or more embodiments, a sampling chamber 34 is positioned between the first and second internal channels, wherein the sampling chamber 34 is defined by a planar surface 62 having a cylindrical sidewall 64 projecting therefrom, wherein an edge of said circular sidewall 64 defines a second aperture 46 configured to receive a portion 20' of a sensor 20. In one or more embodiments, the sidewall may comprise a shape other than cylindrical, such as square or any other suitable shape without departing from the scope of the present disclosure. The sidewall of the sampling chamber may also be nonplanar without departing from the scope of the resent disclosure. In one or more embodiments, the sidewall may be smooth, grooved, or textured.

In some embodiments, an external sensor compartment 36 configured to receive the sensor 20 may be provided, wherein the external sensor compartment 36 is in fluid communication with the sampling chamber 34 via the second aperture 46. Internal sensor compartments are also envisioned. In the embodiments depicted in FIGS. 11-13, the second aperture 46 is oriented orthogonally to the first, or upper, aperture 54. However, in various embodiments within the scope of the present disclosure, the angular relationship between the first and second apertures may be less than or greater than ninety degrees.

In one or more embodiments, an intermediate portion defining a coupling 28 for removably connecting the sensor housing 18 to a wire housing 26 may be provided, wherein the coupling 28 defines a pair of detents 28' for engaging corresponding slots in the wire housing 26. As will be apparent to one of ordinary skill in the art having the benefit of the teachings of the present disclosure, alternative means for connecting the sensor housing to the wire housing are within the scope of the present disclosure.

With continued reference to FIGS. 11-13, one or more embodiments comprise a second end 32 configured for engaging a pump system 12, wherein the second end 32 defines a second substantially planar base portion 70 and a second cylindrical sidewall 72 extending therefrom. In one or more embodiments, the second base portion 70 defines a third, or lower, aperture 74. The third aperture 74 may be parallel to the first, upper, aperture 54. Alternatively, the third aperture 74 may be angled relative to the first aperture 54 within the scope of the present disclosure. In the embodiments depicted in FIGS. 11-13, the second aperture 46 is oriented orthogonally to the third, or lower, aperture 74. However, in various embodiments within the scope of the present disclosure, the angular relationship between the second and third apertures may be less than or greater than ninety degrees.

In the exemplary embodiment depicted, a needle 44 is shown protruding from the third, lower, aperture 74. In one or more embodiments, the needle 44 does not extend beyond the lower connector portion 32 of the sensor housing 18. However, embodiments wherein the needle 44 extends beyond the lower connector portion 32 of the sensor housing 18 are considered to be within the scope of the present disclosure. In one or more embodiments, attaching the second end 32, or lower connector portion, to the pump system 12 results in the needle 44 piercing a pump system reservoir 14, which contains a fluid, thereby enabling the flow of fluid from the pump 12 to the sensor housing 18, and ultimately through the sensor housing 18 to the infusion set 16 affixed to a subject.

One or more embodiments of the present disclosure include a sensor housing comprising a tapered first end defining a first receiver configured for receiving an infusion set tube; the first receiver having a substantially planar base portion and a cylindrical sidewall upstanding therefrom, the base portion defining a first aperture; first and second internal channels in fluid communication with the first receiver via the first aperture, each internal channel having a uniform diameter along its length, wherein the diameter of the first internal channel is greater than the diameter of the second internal channel; a sampling chamber positioned between the first and second internal channels, the sampling chamber defined by a planar surface having a cylindrical sidewall projecting therefrom, an edge of said cylindrical sidewall defining a second aperture configured for receiving a portion of a sensor; an external sensor compartment configured for receiving the sensor, the external sensor compartment in fluid communication with the sampling chamber via the second aperture; a second end configured for engaging a pump system, the second end defining a second substantially planar base portion and a second cylindrical sidewall extending therefrom, the second base portion defining a third aperture, a needle protruding from the third aperture; and an intermediate portion defining a coupling for removably connecting the sensor housing to a wire housing, the coupling having a pair of detents for engaging the wire housing, wherein attaching the second end to the pump system results in the needle piercing a pump system reservoir.

One or more embodiments of the present disclosure include a sensor housing, comprising: a first receiver configured for receiving an infusion set tube; first and second internal channels in fluid communication with the first receiver; a sampling chamber positioned between the first and second internal channels, the sampling chamber defining an aperture configured for receiving a portion of a sensor; and a second receiver configured for engaging a pump system; wherein attaching the second receiver to the pump system results in fluid flow between the sensor housing and a pump system reservoir.

Figure 14:
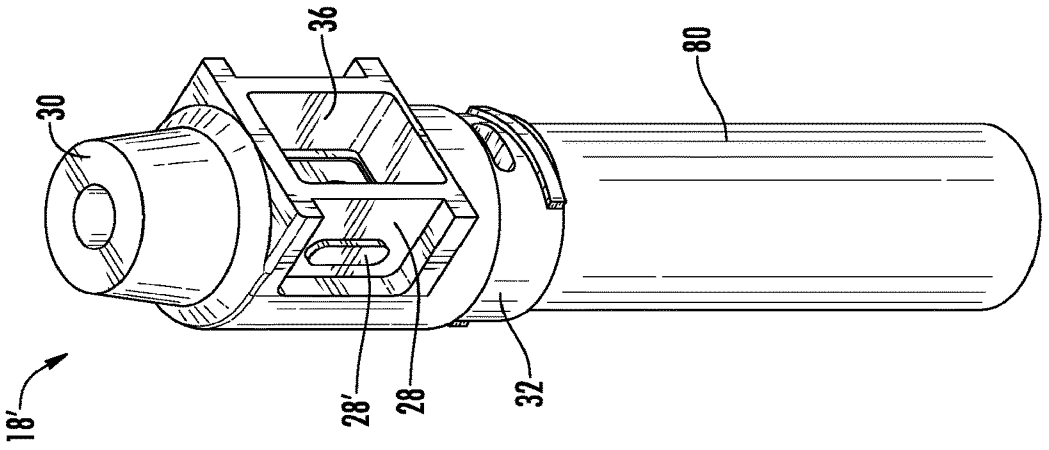
FIG. 14 depicts an alternate exemplary sensor housing.

FIG. 14 depicts an alternative embodiment of a sensor housing 18' having an integrated fluid reservoir. This embodiment of the sensor housing 18' comprises an extended lower portion 80 configured to house a fluid and/or a fluid reservoir therein. Alternatively, the lower portion 80 comprises the reservoir. The extended lower portion 80 is configured to operably connect to a suitable pump system for delivering the fluid in the reservoir through the sensor housing to a subject as herein described in connection with the various embodiments. In another embodiment, a fluid reservoir may have tubing that extends out of the reservoir and constitutes a portion of the flow path. As part of this flow path, there may be a sensor which may be connected in a similar fashion as in FIG. 13 with a sampling chamber somewhere along the tubing that is connected at either side with a fluid path of equal or different diameters which would connect directly to a cannula. The sampling chamber may be connected to a sensor as described herein. In one or more embodiments, the reservoir is an integral part of the pump with all the tubing internal to the device (tubeless/patch insulin pumps). In another embodiment, the reservoir flows directly into the sensing cavity, which is in fluid communication with an infusion set, via a luer-lock system or other connector, that is connected to the patient. In another embodiment, the reservoir, sensor housing, and infusion tubing constitutes one infusion set.

As described hereinabove, and as depicted in FIG. 1B, one or more embodiments of the sensor housing may comprise a first, or upper, connector portion integrally connected to a tube associated with an infusion set. Therefore, one or more embodiments of the present disclosure may include an infusion set comprising a patient interface configured to be removably attached to the patient's skin and delivering a fluid to the patient; a sensor housing in fluid communication with the patient interface; and a tube positioned between the patient interface and the sensor housing. Tubeless embodiments are also envisioned, wherein the sensor housing and patient interface comprise a unitary structure.

In one or more embodiments, the sensor housing comprises any one of the various embodiments of a sensor housing disclosed herein. For example, the sensor housing may comprise a first connector portion configured to connect the sensor housing to the patient interface via a tube; a second connector portion configured to connect the sensor housing to a pump; a sampling cavity positioned between the first connector portion and the second connector portion, wherein the sampling cavity is in fluid communication with the first and second connector portions via first and second channels, respectively, and wherein the first and second channels provide a path for at least one needle, respectively; and a sensor chamber in fluid communication with the sampling chamber, the sensor chamber configured to accommodate a sensor, wherein the sensor measures a value associated with the fluid in the sampling cavity.

Referring again to FIGS. 1-3, an exemplary electronics housing, or kit 22, is illustrated, which includes a housing configured to store the electronic components used to detect infusion set malfunctions. This housing 22 may interact with the sensor housing 18 at the top or other portion thereof via a conductive material (i.e., gold plates, pins, etc.). In one or more embodiments, the housing is configured to clip onto, or cradle, the pump. Alternatively, the housing 22 may be in the form of a sleeve wherein the pump 12 is held, a clamp which engages at least one side of the pump 12, or a clip placed in line between a pump 12 and an infusion set 16. In one or more embodiments, the kit 22 may be independent from the pump and comprise a kit 22 configured to be placed in a location separate from the pump. The electronic components contained within the housing may comprise a microprocessor (not shown) for receiving, monitoring, and/or analyzing data received from the sensor, and a battery (not shown) for providing power to the sensor and other components of the system. The battery may comprise a rechargeable battery. An internal antenna (not shown) for transmitting data from the kit 22 to an external device may also be provided.

In one or more exemplary embodiments, an nRF52 microcontroller uses its 3.3V regulated output to energize an Amphenol NPC-120 Wheatstone bridge based pressure sensor. The output from the sensor is fed to an Analog Devices AD623 instrumentation amplifier which boosts the signal by −34 gain and feeds a signal back to the nRF52 ADC. The ADC input is converted to a psi reading for data acquisition.

In one or more embodiments, the power is turned on and the boot process initializes an SD card and creates a new file with a time stamp from the Real Time Clock "RTC". The main loop begins and records pressure data on one-second intervals. The normal state of the prototype is to take a one hour rolling average of the basal (steady medication flow) pressure. If a bolus (large volume injection) event is started on the pump, a button on the system is pressed until a beep is heard, then the monitoring event is flagged as "bolus" and the basal rolling average is paused until the bolus event is over. The bolus can be ended with a second button press, or a pressure curve monitoring algorithm. If a pressure (or other) reading is outside of the preset parameters during a bolus event, an alarm will sound. There is also a pressure alarm for basal monitoring. Alternatively, the system may require no pressing of any buttons to identify a delivery event and can detect fluid delivery. In one or more embodiments, the system will actively read basal pressure rates and monitor for any sensor readings outside of the acceptable parameters. If sensor readings are outside parameters, this will trigger a notification/alert to the user and/or third party. In another embodiment, this alert system can detect any type of issue/malfunction including, but not limited to, a leak at the infusion site, block at the infusion site, a block in the infusion set, a malfunction of the pump, a kink in the infusion set cannula, a dislodgment of the cannula, any hypertrophic, damaged, or inflamed tissue associated with the infusion/injection site, based on the interpreted pressure readings.

Figure 15:
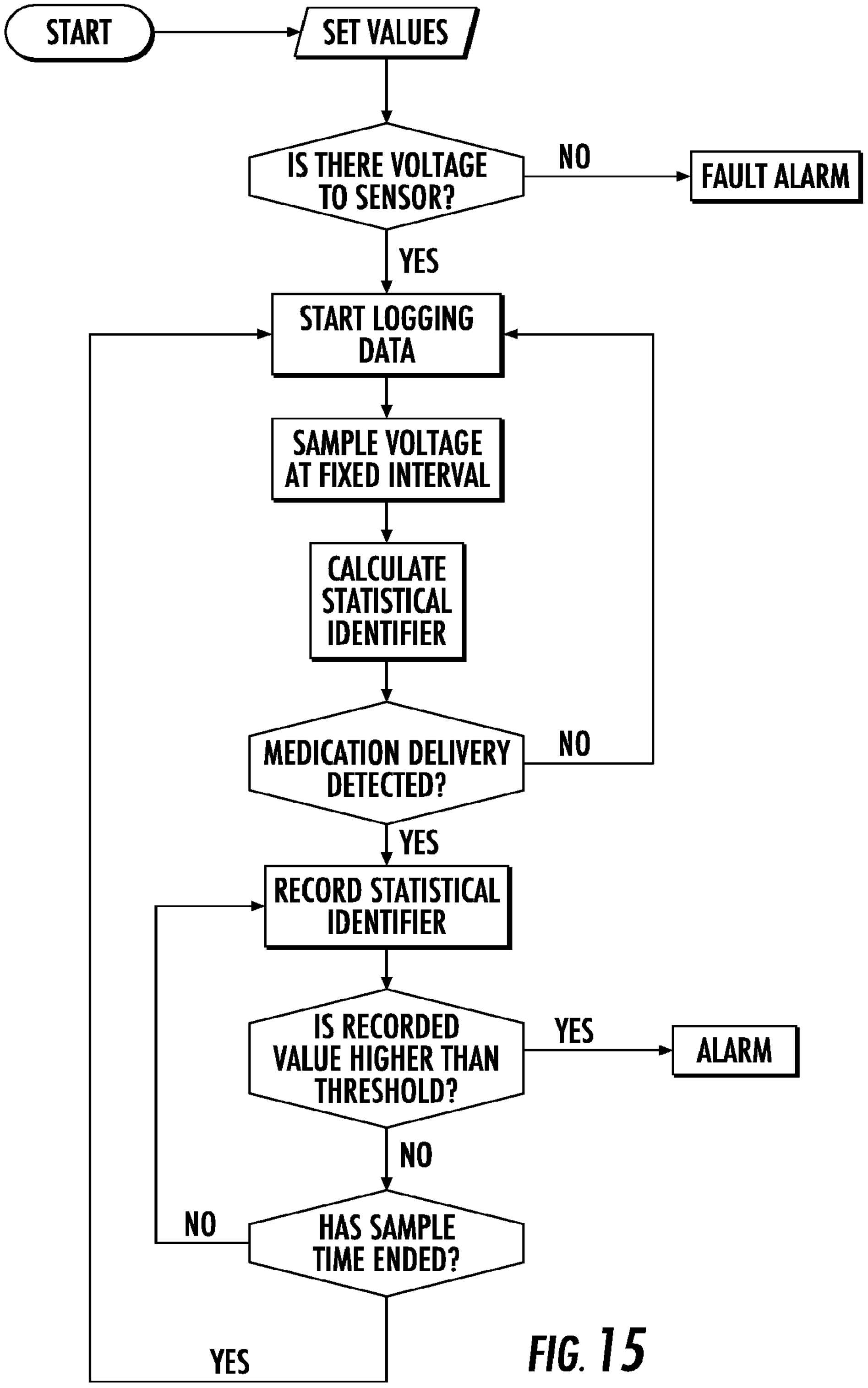
FIG. 15 depicts a flow chart of a method for detecting one or more malfunctions in an infusion pump in accordance with one or more embodiments of the disclosed technology.
Figure 16:
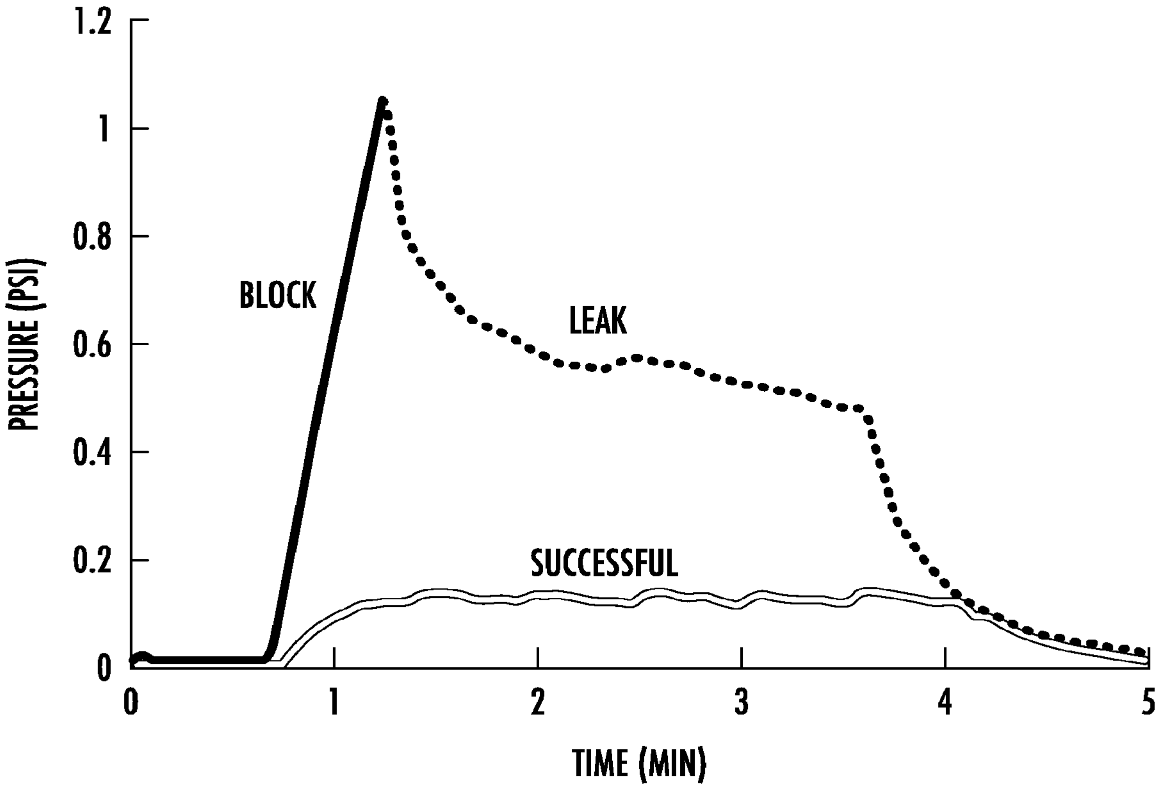
FIG. 16 depicts exemplary data provided in accordance with systems and methods of the present disclosure.

FIG. 15 depicts an exemplary method in accordance with the present disclosure for detecting malfunctions in a fluid delivery system. Alternative embodiments may comprise a method for detecting viability of injection sites not only for insulin injections, but any form of medication which requires medicine diffusing into a patient intradermally or subcutaneously. At the outset, the system may accept input values from past evaluations, which may include but are not limited to tolerable tissue back pressure, diffusion rate associated with back pressure, flow approximation, a maximum value of the tissue back pressure, a minimum value of tissue back pressure, a rate of change associated with medication delivery (e.g., rate of pressure change), an average of any such values, or a percent deviation from any such values. These values may be input by a user, such as a patient's endocrinologist or the manufacturer of the system during the manufacturing process of the device. Alternatively, these input values may change over time based on a user's historical data, variations in treatment, or suggested alternatives from the system better personalized to the user's anatomical, biochemical, or pharmacological variations throughout use of the device. Input values may be altered or reset by a user, physician, or manufacturer to best address the needs of the patient. After values have been input and the system is "on," the device may identify whether a clear power reading is coming from the sensor, e.g., in the form of an electrical reading (voltage, mA, etc.), an auditory signal, tactile signal, and/or manual confirmation. In one or more embodiments, the system may assess the sensor's length of use (duration of time since initial use) and determine whether or not to accept the use of said sensor system.

If the system is operating as intended (e.g., sensor is connected and viable) the path may continue to the next block. If the system is not operating as intended, a fault alarm may occur which may for example include a visual indicator, audio indicator, tactile indicator, Bluetooth™ notification, radio transmission (i.e., phone call, text), a transmittable message to an internet of things (IoT) device or other suitable alarm or alert.

Upon system initialization, the system may take m values at a predetermined rate (e.g., one second, five seconds, etc.). The values can be any one or more of the ones listed above (e.g., electrical, tactile, audible, etc.). These readings may undergo an analysis which will determine values of interest (e.g., max pressure, min pressure, average pressure, etc.). With the values detected, the system may decide whether a predetermined amount of fluid, such as insulin or any other medication, has been delivered and/or is being delivered.

In another embodiment, the system may, based on the detected values, decide whether it benefits the user to inject the medication delivery device into the same infusion/injection site or body region associated with the site, and may suggest another body region associated with infusion/injection sites to be utilized. This functionality may be used to assess and map viable/unviable injection/infusion sites. In one example of a process for selecting, assessing, and potentially switching an infusion site based on the above embodiments, a "System Initialization" stage may include verifying pump and sensor functionality, and preloading of baseline values and parameters. A "Site Selection" stage may include user selection of a site for infusion, wherein the system logs this selection and potentially provides feedback based on past site performance. In an "Infusion Initialization" stage the pump initiates infusion, further recording baseline and injection profile data. A "Site Performance Evaluation" stage may include continuous evaluation of site performance, using metrics from the pump, CGM data, and any additional sources (e.g., environmental sensors or user feedback). If performance is outside of acceptable ranges, the system flags the site as "unhealthy" and alerts the user. In an "Infusion Failure Detection" stage, if an infusion failure is detected the system may classify it (as occlusion, a leak, etc.), alerts the user, and logs the event and associated data. In a "Site Switch Recommendation" stage, if an infusion failure is unresolvable, or if site performance is consistently poor, the system may recommend a site switch, potentially suggesting an optimal new site based on past performance and site rotation guidelines. In a "Site Re-insertion and Assessment" stage, the user may re-insert the pump at a new site, wherein system assessment of the new site takes place. In a "Long-Term Site Performance Logging" stage, the system may log all site performance data for long-term use, which can guide future site selection and provide insights on infusion site health over time.

If no bolus or other defect/malfunction in the delivery of the fluid is detected, the system may remain in its data sampling mode. Otherwise, the system may initialize the next block. When the system enters this next loop, it may begin calculating values of interest. These values may include but are not limited to average pressure reading, max pressure reading, min pressure reading, estimated fluid flow, value rate of change, or duration. If the values found/calculated are higher than acceptable an alarm may be triggered. This alarm may be in the forms listed above (i.e., audible, Bluetooth™, visual, tactile, etc.). If no value is found to be outside of its accepted amount, the system may assess if enough time has passed or if the value found are within a "safe" range, e.g., within an acceptable tolerance, such as a set standard deviation calculated from historical user data or defined by physician or manufacturer. If yes, then the system may return to its data logging mode. As used herein, "value/values" refers to any number or calculated amount determined by the system or number assigned to any electrical, tactile, audible, or frequency identified by the system.

Thus, one or more embodiments of the present disclosure comprise a method for monitoring characteristics of a fluid being delivered and detecting abnormalities within an infusion set and at an infusion site, the method comprising: inputting base values into a processor, the base values comprising a tolerable back pressure, a diffusion rate associated with said back pressure, a flow rate approximation, a maximum permissible back pressure, a minimum permissible back pressure, a rate of pressure change, and/or a percent deviation of the same; identifying a presence of a voltage to a sensor, wherein the presence of a voltage initiates a logging of data, and wherein the absence of a voltage triggers an alarm; logging data at a predetermined interval; the logging comprising sampling the voltage to the sensor at a predetermined interval; calculating, by the processor, a statistical identifier associated with a value of interest, the value of interest being a maximum pressure, minimum pressure, and/or average pressure; determining, based on the statistical identifier, a medication delivery event, wherein a negative medication delivery event triggers the system to return to the logging step, and wherein a positive medication delivery event triggers the system to record a statistical identifier; and determining, by a processor, whether the statistical identifier is greater than or less than a predetermined threshold (such as, in one or more non-limiting exemplary embodiments, a range or standard deviation from a predetermined value), wherein if the statistical identifier is outside an acceptable predetermined threshold, the system triggers an alarm, and wherein if the statistical identifier is within the predetermined threshold, determining, by a processor, whether a sample time has ended.

One or more embodiments of the present disclosure may also comprise: pairing an infusion set or other medication delivery device with a mobile app via BLE, radio frequency, or Wi-Fi; initiating a calibration sequence with no medication flowing through line; entering an infusion site location on a mobile app; measuring, with a sensor, data from a fluid channel (before, during, and after medication flow has begun); sending data from the sensor to a microcontroller (continuously or after being prompted by the user); analyzing, by the microcontroller, the data and deciding if an infusion process is normal or abnormal; wherein if normal, repeating at least one of the prior steps, and wherein if abnormal, alerting, by the microcontroller or some other alarm delivery device, the user through an auditory, visual, or haptic signal; sending, by the microcontroller or other transmitter, information to the mobile device application through Bluetooth™ or other communication technology.

In one or more embodiments, a mobile device application will store infusion data relating to performance of the infusion site, including but not limited to where abnormal infusions are occurring on the patient's body and be able to suggest better infusions sites for the patient to use. In one or more embodiments, a mobile app will connect to the microcontroller or other component in the electronic kit housing and alert the patient and/or caregiver of injection site malfunctions through SMS message or Push Notifications. In another embodiment, the sensor housing stores the infusion data and the mobile app connects with the sensor housing electronics to alert patients to malfunctions.

One or more embodiments of the present disclosure may also comprise: turning on the sensor system; detecting, with the system, no medication flow and initiating a calibration sequence; receiving, by the sensor, data from a fluid channel (before, during, and after medication flow has begun); sending, by the sensor, data to a microcontroller (continuously or after being prompted by the user); analyzing, by the microcontroller, the data and deciding if infusion process is normal or abnormal, wherein if normal, repeating at least one of the prior steps, and wherein if abnormal, alerting, by the microcontroller or other alarm delivery device, the user through an auditory, visual, or haptic signal; logging and/or storing data at various intervals; and exporting the data to a physician or other third party for evaluation.

In one or more embodiments, a sensor reading is used to at least one of estimate or calculate absorption of fluid delivered intradermally or subcutaneously. Absorption estimates and/or rates may be used to estimate the amount of insulin received by the user/patient, identify leaks, identify occlusions, identify infusion site problems, assess infusion site status, identify cannula dislodgement, and identify and/or assess a user's active state (i.e., whether the user is exercising or has an elevated heart rate).

Exemplary parameters measured by the system may include, but are not limited to, full width at half maximum value, maximum value, minimum value, average value, moving average, median value, slope, area under a curve, regression, time to peak, and time to rise.

In one or more embodiments, the TCP protocol comprises: measuring pressure with the fluid line empty of any liquid, wherein a measured pressure may be considered the atmospheric pressure reading (baseline reading); measuring a pressure of the fluid during priming of the line (air pressure) and establishing baseline line pressure with fluid; measuring a pressure of fluid during infusion into tissue (infusion pressure); and calculating TCP by taking the difference of infusion pressure, air pressure, and atmospheric pressure (TCP=Infusion Pressure−In-line Pressure (priming pressure)−Baseline Pressure (Atmospheric).

In one or more embodiments, a protocol for identifying a health of medium and identity of medium comprises the following definitions: Healthy Site—a site where normal use has been classified and has minimal failure percentage and can be classified through CGM data; Unhealthy Site—a site where normal use has been characterized and current performance is outside of acceptable tolerance (may require historical patient data to classify or large data set) and can be classified through CGM data; Good Site—site with low failure percentage (may require patient data for this demarcation); Bad Site—site with high failure percentage (may require patient data for this demarcation); Difference between Unhealthy Site and Bad Site—Unhealthy has been classified as such due to historical patient data and "Normal/

Healthy" has been characterized, Bad-Site is a site with a high rate of failure. Furthermore, the health of a site may be assessed by its continuous ability to absorb insulin which may be estimated by the measurable impact the infusion had on blood glucose (measured effect=BG(t)−BG(0); where t=any time after an insulin infusion, 0=time at infusion) or via other metrics such as the user's daily average blood glucose, time-in-range—time spent within specific threshold (i.e., <70 mg/dL=below range, 70-180 mg/dL=target range, >180 mg/dL)—or the relative difference between a predicted blood glucose value (from an algorithm) and the actual blood glucose value (read from a CGM sensor or blood glucose meter). Identification of an unhealthy site may also occur by a historical analysis of baseline pressure (or other value such as flow, impedance, force, etc.) values at the site while there are no infusions occurring or assessment of select time windows of interest including but not limited to −t seconds prior to an infusion vs t seconds after an infusion where t can be any amount of time or a rolling window of t=k to t_l=t+n where k can be a current time (i.e. 12:00:00 pm) and n is a set value (i.e. 5 mins) resulting in a time window of t to t_l of 12:00:00 μm to 12:05:00 pm then t=t_l and t_l is set again to t+n In one or more embodiments, a method for data acquisition for a new patient comprises: checking a sensor status, a functionality, and/or pairing with a device; preloading manufacturer limits for failure (extreme failure limits determined through clinical trials, experimentation, or other); establishing baseline infusion set measurements (no fluid and primed); choosing an infusion site; initiating injection into the infusion site; recording an injection profile; establishing baseline measurements from site; determining if site is within an operational tolerance (no initial kink or block) [may require waiting period before bolus]; allowing a waiting period; detecting bolus entered into pump; registering, by the system, the bolus via connection to pump and/or determination of flow via statistical identifier; logging data for inputted site, wherein if bolus is finalized without any failure or warning, logging as successful bolus; and wherein if bolus is finalized with a failure or readings outside of acceptable preloaded tolerances, have user examine site and flag; repeating monitor and detection steps for entirety of use period, wherein if site fails throughout use period, flag failure, flag site, and record failure statistical identifiers (time to peak, max, min, FWHM, etc.), and wherein if site does not fail throughout use period, log as successful site and record statistical identifiers (time to peak, max, min, FWHM, etc.).

In one or more embodiments, a method for site mapping for a long-term user comprises: checking sensor status, functionality, and/or pairing with device; loading manufacturer limits for failure (extreme failure limits determined through clinical trials, experimentation, or other) corrected using historical patient data; establishing baseline infusion set measurements (no fluid and primed); choosing an infusion site; injecting into infusion site; logging and analyzing cannula injection profile; establishing baseline measurements from site; determining if site is within operational tolerance (no initial kink or block) [may require waiting period before bolus]; allow a waiting period; entering bolus into pump; registering bolus via connection to pump and/or determination of flow via statistical identifier; beginning data logging for inputted site; monitoring bolus and analyzing using historical statistical identifier for specific site, wherein if within acceptable tolerance, do nothing and continue to record statistical identifier for current use period, and wherein if not within acceptable tolerance, flagging bolus event and comparing to other sites, wherein if outside of tolerance for chosen site and other sites, notifying user and recommending a new site; changing flag to potential bad site, wherein if adverse event occurs through wear time (failure like kink or leak or blood glucose grossly outside tolerance), marking as failed site; logging data for failure type and failed site, wherein if fail percentage is above x %, flagging as bad site and avoiding use, and wherein if fail rate is determined to be because of user error (dislodgement or environmental error) flagging site as such, but do not record failure data.

In one or more embodiments, a healthy site will have low failed use periods and tolerable blood glucose levels. Likewise, an unhealthy site may involve poor infusion profiles at the edge of tolerance and possibly poor blood glucose levels. In one or more embodiments, thresholds of tolerances (optimal, acceptable, borderline {unsuccessful bolus y % of the time but not as bad as z % of the time, for example x %>y %<z %}, and outside of tolerance}). Historical data sets for each patient may aid in finding what unhealthy sites are like, characterize them, and pre-load values into device for evaluation.

In one or more embodiments, a system for considering the hydration level of the patient as a factor in the assessment of the health of an infusion site is disclosed. The system may utilize direct or indirect metrics to determine the patient's hydration level, such as skin elasticity, bioelectrical impedance analysis, or fluid intake reported by the patient. The hydration level may influence the absorption rate of insulin and can also affect the viability of the infusion site. These factors may be incorporated into the assessment of the infusion site's health and the decision-making process for site rotation.

In one or more embodiments, a method for assessing the integrity of the skin at the infusion site is disclosed. This method may utilize external sensors or imaging technologies to evaluate parameters such as skin texture, elasticity, or presence of scar tissue. These evaluations may then be used to determine the viability of a site for infusion, as poor skin integrity may impact infusion success and user comfort. Data on skin integrity may also be logged for long-term monitoring of skin health across multiple infusion sites.

In one or more embodiments, a system-assisted site rotation protocol is disclosed. The system may guide the user in selecting a new infusion site based on a predetermined rotation schedule, the past performance of various sites, and other factors such as skin integrity or hydration level. This system-assisted site rotation aims to ensure that sites are given adequate rest between infusions, helping to maintain skin integrity and improve the overall performance of infusions.

In one or more embodiments, a method for integrating patient feedback into the assessment of infusion sites is disclosed. Patients may report subjective experiences such as pain, discomfort, or ease of use for each infusion site. The system may incorporate this feedback into the overall assessment of site health and performance. This patient-reported data provides an additional layer of insight, capturing information that may not be picked up by existing metrics.

In one or more embodiments, a system for incorporating environmental data into infusion site assessment and pump performance is disclosed. This system may gather data on factors such as temperature, humidity, or barometric pressure, either through inbuilt sensors or through integration with external devices or databases. Environmental factors can potentially affect insulin absorption, pump functionality, or skin health at the infusion site, and thus are important to consider in the overall system assessment.

As previously noted, variations from the described embodiments may exist without departing from the scope of the claims. For example, fluid pressure sensing could be incorporated into a reservoir of a pump or directly at an infusion site. Another embodiment may comprise inserting a membrane inside a sensor housing that can deform with fluid pressure, wherein deformity can be correlated to a fluid pressure reading.

Any material that is biocompatible can be used as the sensor housing material, such as a polymer like polycarbonate. The conductive plate used to provide power to the sensor housing from the electronic kit can be made of any suitable conductive material. The placement of the electronic kit can be adjacent to the sensor housing as opposed to on the back of the insulin pump. The sensor could eventually become part of the blueprint of future insulin pump models and can easily be incorporated within the electronics and housing of the pump. Thus, it is seen that apparatus and methods are provided for detecting one or more malfunctions related to an infusion pump.

Although particular embodiments have been disclosed herein in detail, this has been done for purposes of illustration only, and is not intended to be limiting with respect to the scope of an invention as disclosed herein. In particular, it is contemplated by the inventors that various substitutions, alterations, and modifications may be made without departing from the spirit and scope of the disclosed technology.

Exemplary, non-limiting, modifications to one or more of the embodiments disclosed herein may include placing the sensor and/or sensor housing anywhere along the fluid path, such as, for example, connected to the reservoir or placed inside the pod portion (e.g., patient interface) of an infusion set near the infusion site. Alternatively, the sensor could be embedded into the infusion pump, so it has contact with the reservoir. The sensor could also be imbedded into the pod portion of an infusion set close to the needle injector and tubing connector.

In one or more embodiments, the sensor could be imbedded into "patch pumps" as long as it is in contact with the fluid line. The sensor could be imbedded into an injection pen close to the tip of the injector as long as it is contact with some type of fluid.

In one or more embodiments, the tubing material could be a material that expands and contracts with medication flow, wherein a deformation of the tubing triggers an electrical signal which can be read, interpreted, and used to evaluate medication flow.

In one or more embodiments, the microcontroller could be placed in a housing that connects to any point on the external part of an infusion pump. The microcontroller may be in a standalone box that does not have any connecting wires. In another embodiment, the microcontroller may be in standalone box that has one wire that connects to an electrical outlet. In yet another embodiment, the microcontroller may be placed inside the infusion pump, thereby eliminating the need for an external attachment (i.e., electronics kit).

In one or more embodiments, the sensor could be directly connected to a microcontroller through the use of wires. Alternatively, the sensor could connect to a microcontroller through use of Bluetooth Low Energy (BLE). In yet another embodiment, the sensor can connect to the microcontroller via fiber optic cable, conductive plate, or conductive gel to relay data. In another embodiment, the sensor and microcontroller could be part of the same electric board inside the sensor housing. In another embodiment, the sensor, microcontroller, and infusion pump circuitry can be part of the same electric board.

In one or more embodiments, the microcontroller may connect to a mobile device through the use of Bluetooth Low Energy (BLE). Alternatively, the microcontroller could connect to a mobile device through the use of Wi-Fi or radiofrequency. In yet another embodiment, the mobile device may be connected through BLE, Wi-Fi, or radio frequency and the data is sent in data sets through an internet portal. Data may be sent continuously or on demand by the user.

In one or more embodiments, the sensor could be used to measure pressure in the fluid line or a rate of fluid infusion. Sensing may also be done through an electrical chemical change. Tactile sensing may also be incorporated to evaluate when the pump is operational and flowing medication. There may also be a sound sensor, which registers the audible noise from the pumps motor and uses it to evaluate flow. Another embodiment may comprise inserting a membrane inside the in-line fluid sensor that can deform with fluid pressure, and the deformity can be correlated to a fluid pressure reading.

Any material that is biocompatible can be used as the housing material, such as polycarbonate. Different types of sensors configured for measuring pressure, flow rate, humidity, temperature, ultrasound, impedance, ion levels, etc. are also within the scope of the present disclosure.

In one or more embodiments, the data from the sensor may be stored on an external storage device such as, for example, a microSD card within the microcontroller system. The data may also be sent to cloud storage where it could connect to a data storage server and be encrypted for security purposes. The data may also be sent to health data cloud services that are currently in the market, such as Glooko, through the internet. Data may also be stored on a paired electronic device (e.g., smartphone).

The sensor may be powered through the use of wires to an external battery near the microcontroller. If the electronics kit is independent (not directly connected) of the sensor, then the infusion set can be connected to a power source via conductive plate (metal, chemical, etc.) to supply power to sensor. A battery may be included in the sensor housing to provide power directly to the sensor. The sensor may also be powered by a battery that converts mechanical movement of patient into electrical power. The sensor may also be powered by a detachable battery separate from the electronics housing which connects via magnets, conductive plates, or cables and can charge by directly connecting to the sensor or via induction charging. In one or more embodiments, the sensor may be powered by the energy of the infusion pump itself.

The microcontroller may be powered by a battery on the same circuit board inside the housing that is connected to the back of the infusion pump. The microcontroller may be powered by an electrical outlet if it was a part of standalone box. The microcontroller may be powered by a battery that converts mechanical movement of patient into electrical power. The microcontroller may be powered by the infusion pump itself.

The embodiments disclosed herein may be utilized with many different types of infusion pumps, including but not limited to, those used for treating diabetes, cancer, pregnancy, and delivering IV medication. The algorithms disclosed herein may be integrated into future infusion pump software. Embodiments herein may be used with multi-medication infusion pumps (e.g., a pump that dispenses at least two medications via at least two infusion sets or dual chamber tube; pumps that dispense more than one medication without external tubing like Omnipod). The embodiments disclosed herein are not limited to the use of external tubing, and may also be used in connection with internally housed medication dispensing pumps. Embodiments herein may be utilized at the same infusion site as continuous glucose monitors (CGMs) in-line with the medication fluid. Embodiments herein may be utilized with stationary or ambulatory infusion pumps. Alternatively, embodiments herein may be integrated with injection pens, syringes, and the like as they inject a fluid into intradermal or subcutaneous tissue.

In one or more embodiments, a medication injection pen comprises at least one integrated sensor capable of monitoring fluid delivery and detecting abnormalities with the injection or the injection site. The type of sensor used in this configuration may include, but is not limited to, a force sensor, a duration sensor, a bioimpedance sensor, a flow sensor, or any combination thereof.

In some embodiments, a force sensor may be embedded into the push-button mechanism of the pen, allowing for continuous monitoring of the force applied during an injection process. In the event of a force higher than the average user-applied force, as detected by the force sensor, a difficulty with the injection process such as a blocked needle or a hardened skin site may be inferred.

Alternatively or additionally, a duration sensor may be incorporated within the pen, which may be a simple timing mechanism triggered by the initiation and completion of the medication delivery process. If the injection time, as tracked by the duration sensor, exceeds a predefined limit, an issue with the medication delivery, such as an occlusion or a partial blockage, may be suspected.

In yet another embodiment, a bioimpedance sensor may be integrated into the needle of the pen. This sensor may function by transmitting a small electrical current through the tissue at the injection site and subsequently measuring the resulting impedance, thereby providing data indicative of the tissue's hydration level, the presence of subcutaneous fat, or other physiological parameters that may influence the absorption and effectiveness of the medication.

In yet another embodiment, a flow sensor may be situated within the pen's cartridge, allowing for direct measurement of the rate of medication movement. Significant deviations from the standard flow rate, as measured by the flow sensor, may be indicative of an issue with the medication delivery or the injection site.

The injection pen may further comprise a built-in memory module for storing data derived from the aforementioned sensors. In the absence of such a module, the sensor data may be transmitted to a connected device, such as a smartphone, tablet, or computer, via a wireless protocol including but not limited to Bluetooth, Wi-Fi, NFC, or any other suitable wireless communication protocol. A wireless communication module, when present, may be integrated into the body of the pen, where it does not interfere with the injection process.

The connected device may be equipped with a dedicated application capable of receiving, storing, and analyzing the sensor data in real-time or retrospectively. This application may alert the user of any detected issues during an injection and track trends and patterns over time, thereby facilitating informed decision-making and effective problem resolution. The sensor data may also, with user consent, be uploaded to a secure cloud server for further analysis, historical trend identification, long-term storage, or sharing with healthcare providers.

In one or more embodiments, the systems, methods, and algorithms outlined for an ambulatory insulin pump can be equally applied to a medication injection pen, as would be understood by one skilled in the art. This includes, but is not limited to, the application of machine learning classifiers for detecting injection site failures, utilizing embedded sensors for monitoring fluid delivery, and incorporating a medication monitoring algorithm to analyze data gathered from these sensors. Additionally, connected device functionality, cloud data storage, and user interface paradigms described for the pump embodiments may also be adapted for use in a pen configuration. Furthermore, the described method for site mapping and health monitoring in pump embodiments can be transposed to the pen embodiment, facilitating optimized site selection and enhanced medication delivery. As with the pump, any improvements or variations in the systems or methods suggested by the system for personalization to the individual's physiological, biochemical, or pharmacological variations may be incorporated into the pen embodiment, offering a customized and efficient user experience. All features described above and throughout the present disclosure can be adapted and implemented in the pen configuration in ways that those skilled in the art would find obvious based on the teachings herein.

Referring next to FIGS. 17-26C, in various embodiments a system and method as disclosed herein may implement a control algorithm aimed at expanding the diagnostics capabilities of current insulin pump technology to function as a more personalized system. The novel algorithm may for example consider real-time and historical data streams from the insulin pump or medication delivery device, CGM, and patient infusion habits and logged events (meals, sleeping, exercise) and combine that with pressure readings from either an externally mounted/retrofitted device or an onboard pressure sensor integrated into the insulin pump, CGM, or other novel device supplemental to treatment. The algorithm may utilize pressure data from onboard devices sensor or other infusion monitoring sensor including, but not limited to, a force sensor, impedance sensor, piezoelectric sensor, flow sensor, distance sensor, etc., and/or may further be expandable to include other types of sensors including, but not limited to, an accelerometer, a gyroscope, heart rate monitor, spO2 monitor, heart rhythm monitoring device (pacemaker, loop recorder, CAM monitor), temperature sensor, impedance sensor, humidity sensor, and the like. These additional data streams may come directly from the therapeutic devices (CGM, insulin pump, medication injection pen) or may be calculated from other data streams or may be obtained via other external devices such as a smart phone connected to cloud systems or networks which, for example, may further obtain geographical weather data from the region of the patient, or supply sensor data from its own respective set of sensors.

An algorithm according to such embodiments may first focus on detection of abnormalities in infusion performance which can include but are not limited to, infusion site failure, infusion set failure, hardware failures, medication delivery failures, environmental failures (extreme heat, extreme cold, animals eating materials, etc.), or any other event which may alter delivery of medical therapy past its documented tolerance range, including but not limited to hardware tolerances (current, voltage, etc.), software tolerances (past the detection/prediction threshold from control algorithms), and the like. Blood glucose (BG) readings may be examined from an external blood sugar monitor (CGM, meter) or from any device which may provide a BG reading (smart contact lens, implantable device, biomarkers, etc.). The system may read this BG value based on a set timing (e.g., x minutes, seconds, nanoseconds, hours, etc.) by the device or any future iteration of the algorithm. The algorithm could also receive information from the patient's insulin pump or any other medication delivery device. This may for example include denoting a start time of the medication delivery, a delivery rate, an actual increase in supplied voltage/current or increase in impedance necessary to actuate the pump to deliver medication or as a result of pump actuation, information about the patient (insulin sensitivity, carb ratio, etc.), any action from the user (prompting medication delivery, meal announcement, exercise announcement, etc.), delivery mode (auto, basal, bolus, etc.), any native alert function from the pump (low battery, no delivery, component failure, etc.), and any other information which the pump may use as part of its normal function. The control algorithm can leverage this data in a comprehensive decision-making module that identifies infusion abnormalities and takes appropriate action based on defined parameters.

Figure 17:
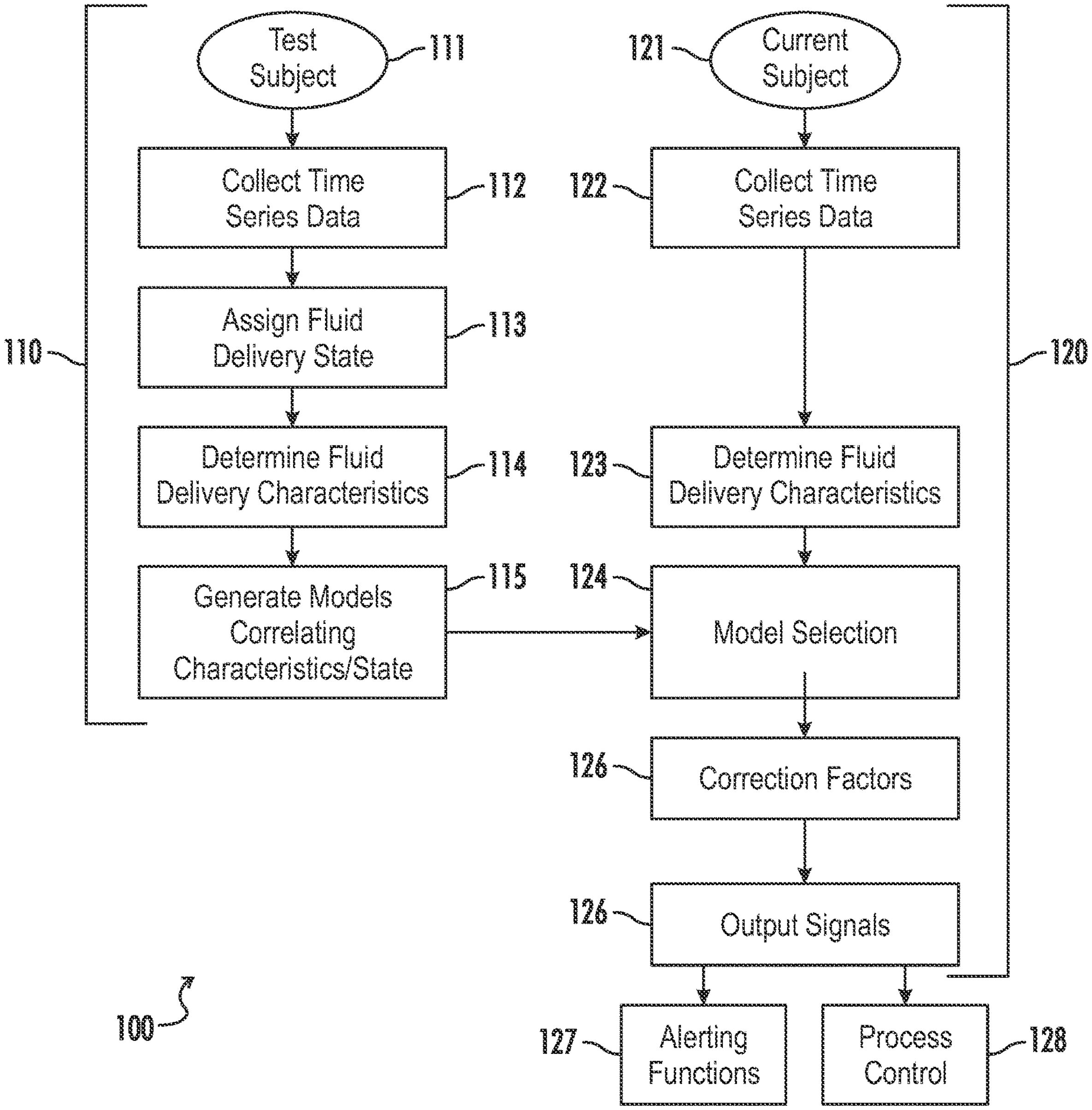
FIG. 17 depicts an exemplary method in accordance with the present disclosure.

Referring particularly to an exemplary method 100 as illustrated in FIG. 17, a model creation and development stage 110 may be provided along with a model implementation state 120. An algorithm as disclosed herein may exist as one model applied in a series of steps or as a combination of processing steps. One of skill in the art may appreciate that there are many ways to create a model/algorithm with applications in hardware. One proposed method involves collecting training and test data 112 to create a machine learning model. The data may be collected from test subjects 111 such as for example human or animal users.

Figure 18:
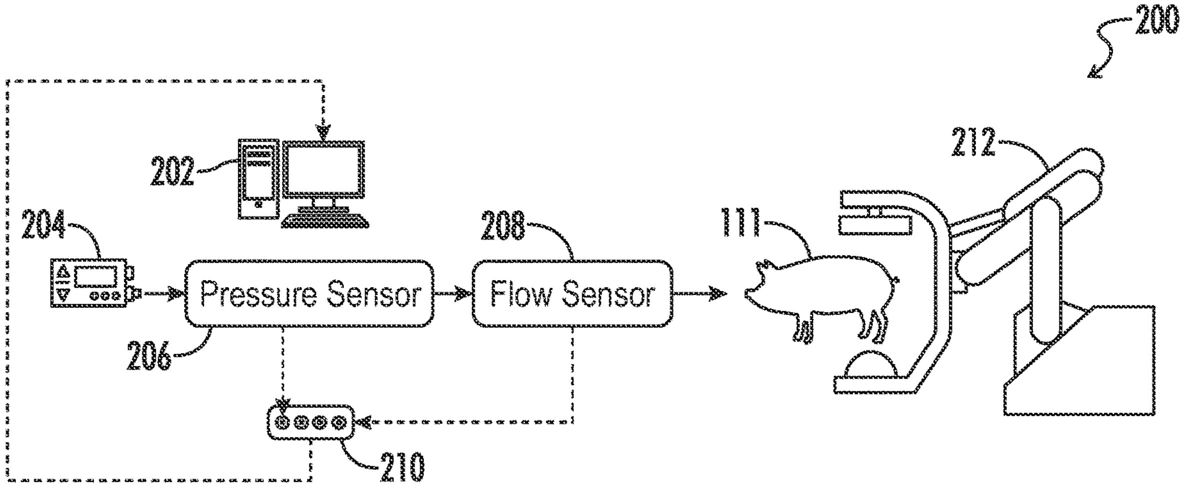
FIG. 18 depicts an exemplary data collection process with respect to a test subject and in accordance with at least the embodiment of FIG. 17.

As represented in FIG. 18, a data collection system 200 using a swine model may include a pump 204, a pressure sensor 206, and a flow sensor 208 connected in-line with the pump 204 and with the distal tip of the infusion line connected to the swine subject 111. The swine subject 111 may be placed on a bed (not shown) positioned to operate with an imaging machine 212 including but not limited to a fluoroscopy unit, a computed tomography scanner, magnetic resonance imaging, or the like. The sensors can be connected to a sensor reader 210 equipped to accept one or multiple signals and connected via a cable to a computer 202. In one or more embodiments, the pump can be an insulin pump, a pump configured to deliver oncology medication, Parkinson's medication, etc. The pump may be configured to deliver medication to various locations including, but not limited to, subcutaneously, intravenously, intraperitoneal, extraperitoneal, intradermally, etc. The pump may not have an exposed infusion line and instead may have an internal line capable of infusing medication via a port. The pump may be a series of pumps configured to work together. The sensors may be configured to be internal to the pump. The sensor reader may be an onboard microcontroller/processor of the pump. The computer may be connected to the sensor reader via a Bluetooth connection, radio frequency connector, Wi-Fi, or another form of wireless communication. The sensor reader may be an external device such as a smartphone or tablet. The data collection may be done completely on the sensor reader instead of a computer. The reading can be done on the pump and transmitted over a wired or wireless connection to a computer, smartphone, or other device. The pressure sensor or flow sensor may be the only sensor used, alone or combination with an altogether different sensor. The sensors may not be inline and can instead be related to the infusion mechanism of the pump such as a force sensor on a reservoir or plunger connected to the pump, a sensor that wraps around the pump or infusion line and is not directly in the flow path.

During data collection an operator may initiate a program on or via the computer to start a data collection program using the sensor reader to read data from the sensors, wherein an operator can program a desired infusion volume onto the pump, the imaging machine can be turned on and image acquisition may begin, the infusion can be started, and data collection is in progress. During the infusion imaging is constantly being collected. Once the infusion is done, the sensors continue to read until a predetermined time is over. Once the total monitoring period is over the imaging machine can take a different type of image such as a three-dimensional (3D) image instead of a two-dimensional (2D) image if the machine is configured for it, or a different imaging setting may be used.

Once the data is collected a fluid delivery state (e.g., label) can be assigned (step 113) to the infusion using the data collected via the sensors and close examination of the imaging acquired during the study.

In one embodiment, an analysis of fluid volume infused vs. expected volume can be used as a metric for defining a successful infusion or failure. In another embodiment the presence of fluid located in the injection target space (subcutaneous or intravenous) can be used as a criterion for normal infusion or failure, wherein imaging data can be used to make this assessment or a segmentation of the imaging data.

In an alternative embodiment, pressure sensor data may be used to label an infusion if the max pressure is above or below an acceptable threshold, or whether the data pattern correlates with a specific label indicative of the infusion state. Furthermore, a visual inspection may also be used to determine if the tubing placed into the subject was compromised in any way. The system could employ a combination of all these techniques to enhance the accuracy and reliability of infusion evaluation. Additionally, the system can gather longitudinal data through separate sensors following the infusion process. For instance, if insulin is being infused, a continuous glucose monitor can be employed to track the patient's response over time. This longitudinal monitoring is not merely for confirming the immediate success of the infusion, but also for understanding and predicting the patient's long-term response to the medication. Importantly, these metrics and measures are not fixed, but can be continually refined and optimized through machine learning algorithms. As the system gathers more data and "experience", it can improve its accuracy in identifying and classifying successful and failed infusions, contributing to a more personalized and effective therapy for each patient.

Figure 19A:
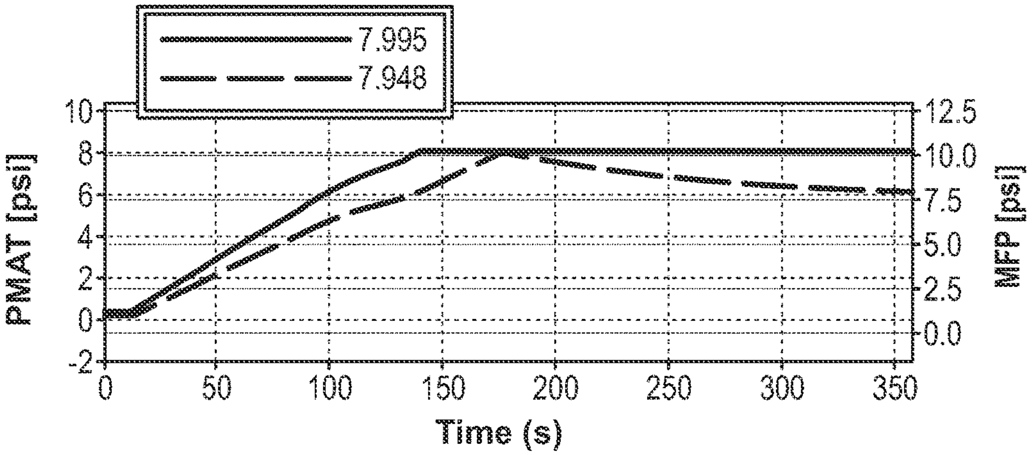
FIGS. 19A and 19B depict a pressure graph and a flow graph, respectively, indicating an exemplary infusion failure.
Figure 19B:
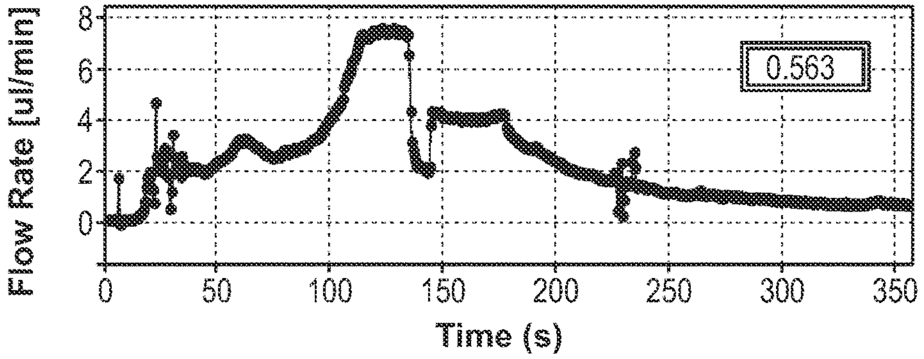

Referring to FIGS. 19A and 19B, for example, a failed infusion has resulted from a kink in the cannula after being pulled out of the infusion site, which may be visually indicated using x-ray images showing a bent and/or a smaller than expected bolus field. The pressure graph of FIG. 19A reveals associated high pressure values and the flow graph of FIG. 19B showcases lower than expected flow rate (expected 15 uL/min average) with a final volume delivered of 13 uL as opposed to an expected 40 uL.

Figure 20A:
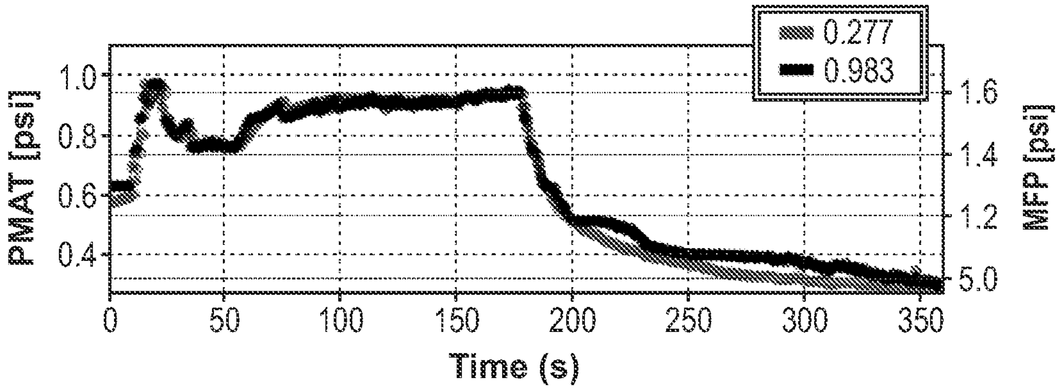
FIGS. 20A and 20B depict a pressure graph and a flow graph, respectively, indicating an exemplary successful infusion.
Figure 20B:
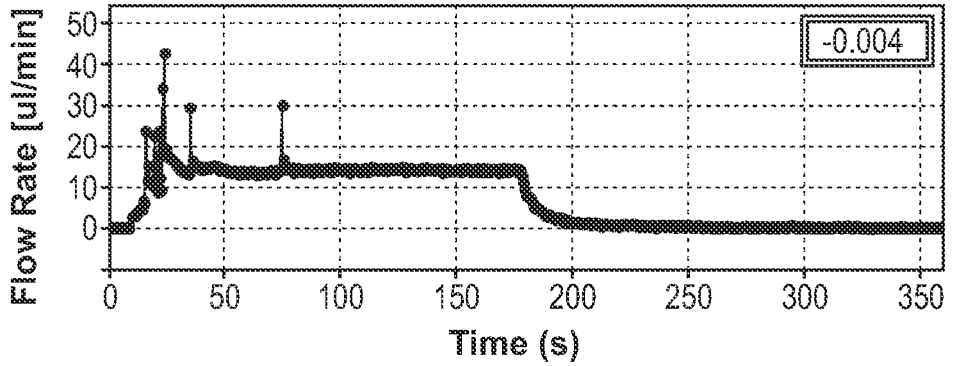

In contrast, a successful infusion site is represented, optionally using standard and/or x-ray images (not shown), via the pressure graph of FIG. 20A which reveals an expected maximum pressure of less than 2 pounds per square inch (PSI), and via the flow graph of FIG. 20B which showcases flow rate with an acceptable average (e.g., expected 15 ul/min average) and with a final volume delivered of 40 uL delivered with respect to a 40 uL target.

Figure 21A:
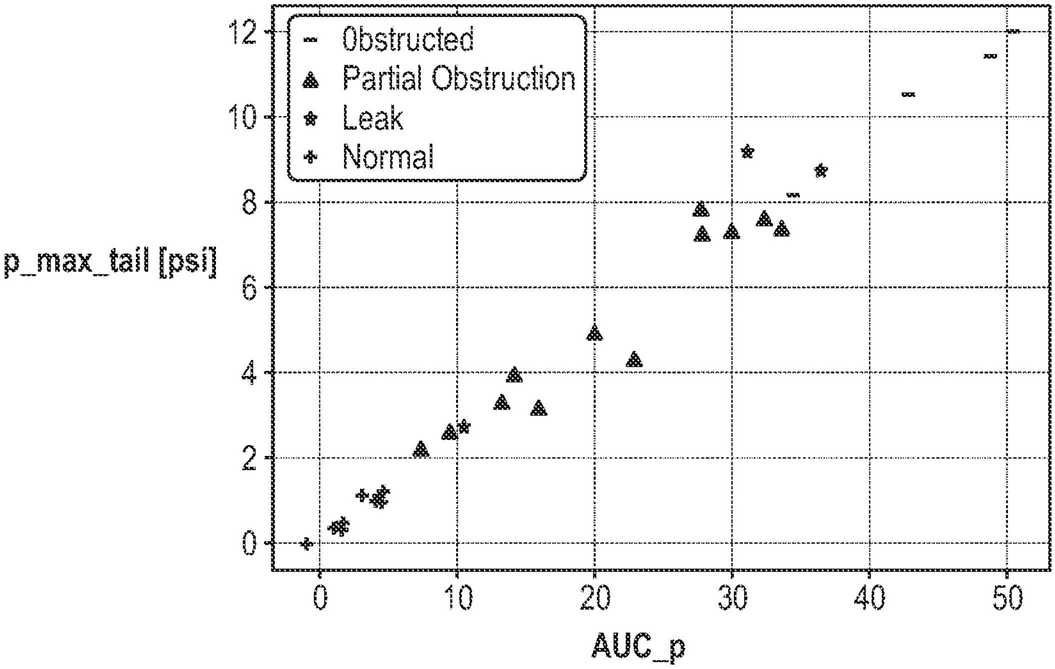
FIGS. 21A and 21B are graphical views representing, respectively, a spread of assigned fluid delivery states (e.g., infusion labels) across two features, and exemplary feature calculations from pressure with respect to time.
Figure 21B:
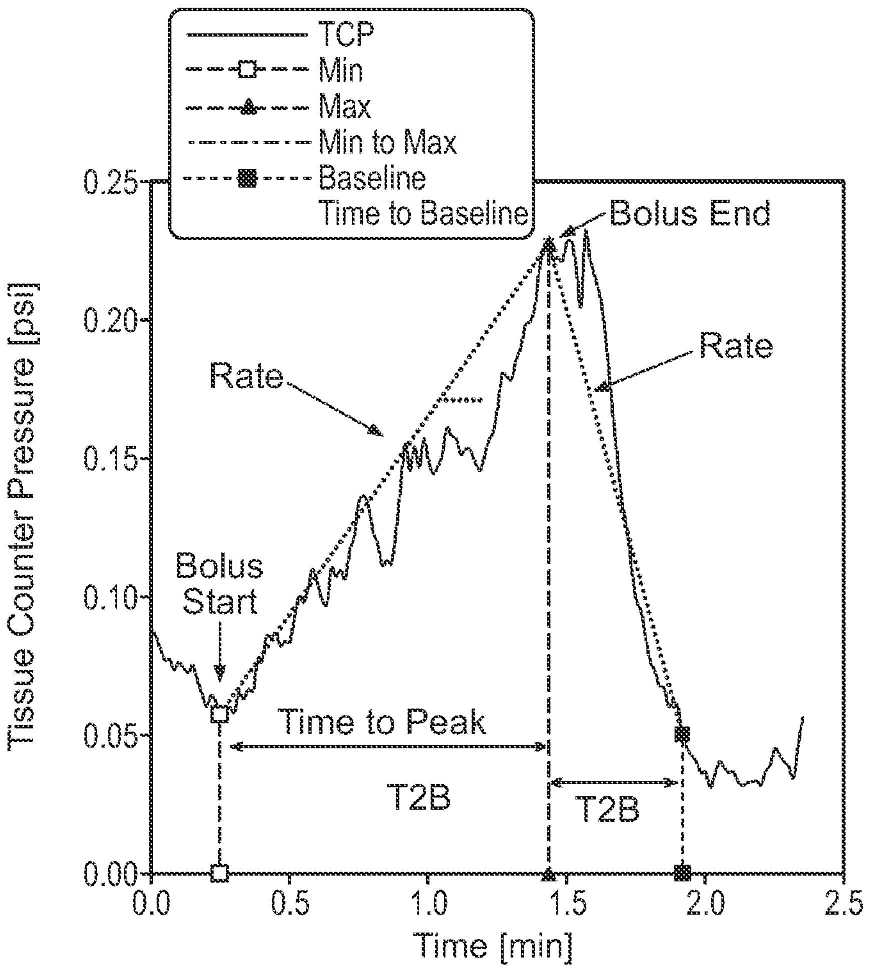
Figure 21C:
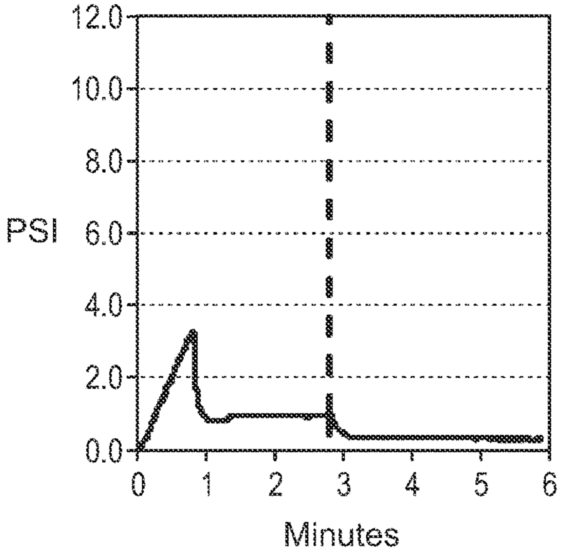
FIGS. 21C to 21F are graphical views representing different fluid delivery states (e.g., infusion labels) with their corresponding pressure tracings highlighting the difference between shapes and magnitudes for the same infusion.
Figure 21D:
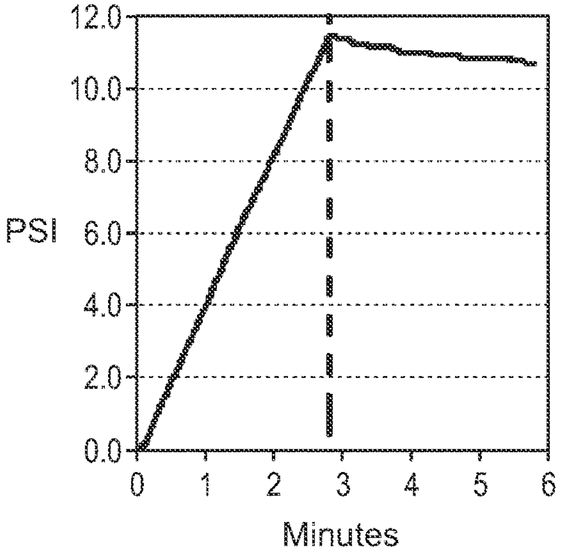
Figure 21E:
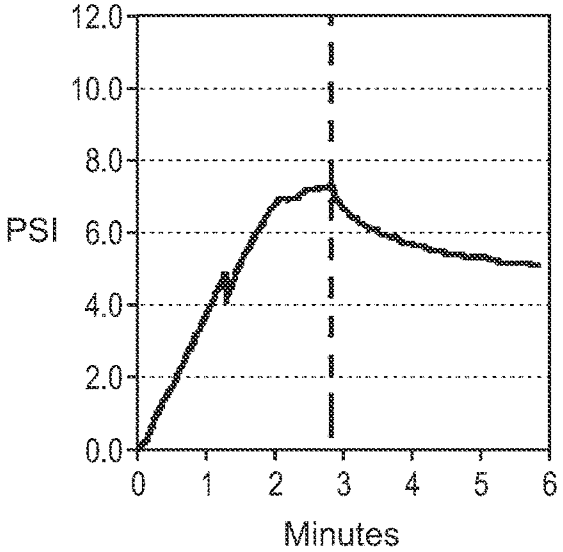
Figure 21F:
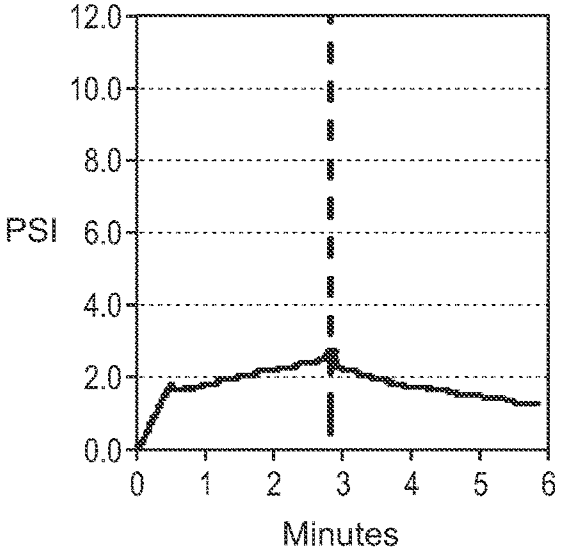

With the label created the model creation and development stage 110 of the method 100 may in various embodiments further include feature creation, also referred to herein as the determining of fluid delivery characteristics (step 114). Within the scope of the present disclosure, "features" may refer to discernable characteristics derived from the time series data collected from various sensors. It is foreseeable that one of skill in the art could construct a unique set of features that correlate with different labels (or fluid delivery states). For example, FIG. 21A illustrates a plot of two features—maximum pressure during the end of the infusion (p_max_tail) and area under the curve for pressure—and further how they correlate with the multi-class labels. FIG. 21B further illustrates exemplary feature calculations for pressure with respect to time, and FIGS. 21C to 21F illustrate different infusion labels with their corresponding pressure tracings to highlight the difference between the shapes and magnitudes for the same 4 U infusion.

Additional features can be created, including but not limited to a maximum pressure of the active infusion region, a time to maximum pressure (time to peak), a rate of increase for maximum pressure, a time to baseline (T2B), and the like.

Figure 22:
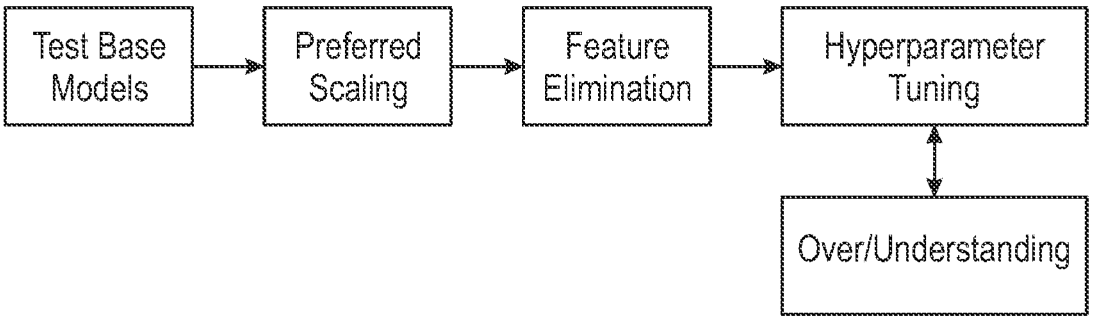
FIG. 22 is a flow diagram representing an exemplary sub-process for identifying a suitable model for failure detection.

After feature creation is completed, an exemplary model creation sub-process 115 may be performed as outlined in FIG. 22. These steps may for example include testing a set of base models, scaling the features and reevaluating, performing feature elimination, reevaluating for the "best" model, and finally performing hyperparameter tubing with an additional step of over/under sampling of the data as needed.

Because the data has been labeled, supervised learning models may be utilized such as support vector machine (SVM), logistic regression (LR), random forest (RF), Naive Bayes (NB), and the like, however unsupervised learning can also/otherwise be used. In an embodiment, a model is selected from a group of classification compatible models, the labeled data is coded to be ordinal instead of categorical, and a group of base models is then tested before dropping one or more of the poorest performing models. In one particular example, the remaining models included SVM, LR, and RF. Scaling can then be performed on the feature set per model type to determine the best scaling technique. Feature elimination may then be performed using recursive feature elimination to reduce the feature set. Finally, hyperparameter tuning was provided using the GridSearchCV Python library with three repeats of 10-fold stratified k-fold cross validation, wherein F2-measure was used for scoring. Adaptive synthetic sampling was performed during training with respect to the minority class. The "best" model was found to be an SVM model, however future testing and training may identify a different model and these results are understood as being merely exemplary.

$$F2\ \text{measure} = \frac{5 * \text{precision} * \text{recall}}{4 * \text{precision} + \text{recall}}$$

$$\text{recall} = \frac{\text{True Positives}}{\text{True Positives} + \text{False Negatives}}$$

$$\text{precision} = \frac{\text{True Positives}}{\text{True Positives} + \text{Fales Positives}}$$

This data collection method may for example be altered for use in live humans via the use of a clinical study. In one or more embodiments, the data collection process may be limited to a benchtop environment where for example an onion is used instead of a swine, or a hydrogel compound may be used to obtain representative infusion data. Furthermore, instead of an off the shelf sensor reading, an ambulatory compatible device may be used, such as an insulin pump or other medication delivery device. These devices could have the capability to read data from multiple sensors, execute onboard data processing, and transmit data to a secondary device. In an additional embodiment, the data processing could be performed on a cloud-based platform, enhancing scalability and access. Other wearable technologies, such as smartwatches or smart clothing, could also be integrated into the system to offer a wider array of data points and improve the comprehensiveness of the system. Methods and models proposed may be adaptable and optimized over time based on real-world performance and ongoing developments in the field.

In an embodiment of a method as disclosed herein a classification model may be deployed into an ambulatory insulin pump system to detect infusion failures. Infusions may be classified as "normal", "occlusion", "partial occlusion", "leak", "dislodgement", "other", etc., leveraging real-time data from multiple data streams, including fluid dynamics data (force, pressure, flow rate, volume), CGM readings, meal logs, exercise logs, sleep logs, and potentially other environmental or physiological data.

For example, the system may initially accept input values from past evaluations. These may include various features derived from the data streams, such as average BG level over the past hour, changes in fluid dynamics measurements, correlations between meal/exercise/sleep events and changes in BG levels or fluid dynamics, and so on. These values may be pre-calculated on the pump itself, on a connected device such as a smartphone, or in the cloud, depending on the system's design and constraints.

Next, the system may check whether the insulin pump and its sensors are functioning correctly. This may involve checking for a clear power reading, assessing the sensor's duration of use, and other checks as needed. If any problems are detected, the system may trigger an alarm via a visual, auditory, tactile, or remote notification (e.g., a smartphone alert or an IoT message).

Once the system is operational, it begins collecting real-time data from its various sensors and sources. It preprocesses this data as necessary to normalize and clean the acquired data, for example, by handling missing values, removing noise, or standardizing values for better comparability and model performance. It then identifies and extracts relevant features from the preprocessed data. This could involve, for example, calculating moving averages or other statistical measures of recent BG levels, identifying changes in fluid dynamics measurements that might signal an occlusion or leak, or identifying correlations between meal/exercise/sleep events and changes in BG levels or fluid dynamics. These features may then be input into the pre-trained classification model.

The model, which may be implemented on the pump itself, on a connected device, or in the cloud, outputs a predicted class for the current infusion. The system interprets this prediction according to a set of predefined rules, for example: if the model predicts "normal", continue regular operation; if the model predicts "occlusion", "partial occlusion", "leak", or "dislodgement", trigger an alert to the user and potentially suspend insulin delivery; and/or if the model predicts "other", trigger a generic alert, and potentially perform further diagnostic checks.

Throughout this process, the system may log all relevant data and predictions. This data can be used to update the model periodically, to adapt the system's rules based on the model's past performance, and to provide feedback to the user via an interface, which could be an app on a smartphone or a display on the pump itself.

The system may continue this loop, periodically evaluating its sensors and collecting, preprocessing, and classifying data until a malfunction is detected or the system is turned off. This allows for continuous, real-time monitoring of infusion conditions and rapid detection of any failures.

Figure 23:
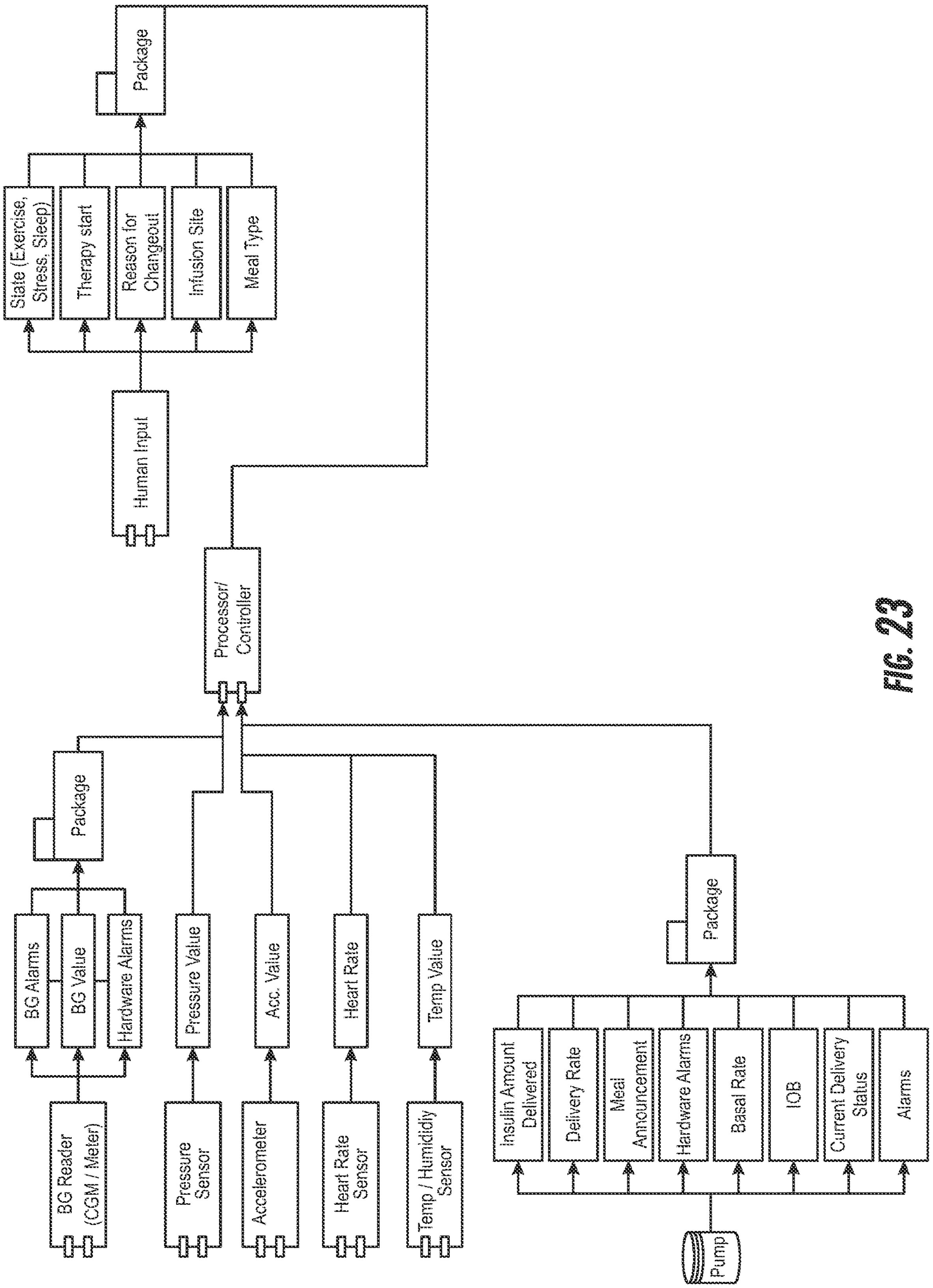
FIG. 23 is a block diagram representing different inputs which may be considered in an exemplary system as disclosed herein.

In various embodiments of a system as disclosed herein, a control module may be provided and in functional communication with various input data sources as represented for example in FIG. 23. The control module may for example be implemented as a software program, an algorithm within or executed by a software program, a physical device such as a microcontroller, a physical device such as a microcontroller with unique software programs and or an algorithm(s), and can be placed either in the device it is responsible for controlling or a secondary device including but not limited to a smartphone, external sensor, daughter board inside a device, etc.

Various embodiments may include logging data to an onboard storage device such as an SD card. System components may be connected to an external computing device via a wire, or may communicate remotely using a wireless communication protocol or over the internet. In an embodiment, a control module may include a box storing a PCB with headers to accept a microcontroller board, a data storage board on one side, and provide support for an on/off switch. On the underside, the PCB may accept a daughter board with an electrical circuit capable of regulating the power delivery and providing a stable voltage reference. Furthermore, the underside of the board may have a battery connector able to secure a replaceable 18650 model battery. External features of the box may support one or more sensor connections compatible with a pressure and flow sensor, user interface tools such as a button, a charging port, etc. On the internal microcontroller, additional sensors may be available such as a gyroscope, accelerometer, magnetometer, temperature sensor, barometric pressure sensor, audio sensor, light sensor, etc. The microcontroller may also support buttons mounted on the board and an LED light. The proposed device may allow for ambulatory use of the sensors without the need for a wired connection to a PC.

The terms "controller" and "microcontroller" as used herein may refer to, be embodied by or otherwise included within a machine, such as a general purpose processor, a digital signal processor (DSP), an application specific integrated circuit (ASIC), a field programmable gate array (FPGA) or other programmable logic devices. These can include processors on a mobile device such as a smartphone, or a processor within a cloud-based computing system. These can include discrete gate or transistor logic, discrete hardware components, or any combination thereof designed and programmed to perform or cause the performance of the functions described herein. A processor can also be implemented as a combination of computing devices, e.g., a combination of a DSP and a microprocessor, a plurality of microprocessors, one or more microprocessors in conjunction with a DSP core, or any other such configuration.

The various illustrative logical blocks, modules, and algorithm steps described in connection with the embodiments disclosed herein can be implemented as electronic hardware, computer software, or combinations of both. To clearly illustrate this interchangeability of hardware and software, various illustrative components, blocks, modules, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

These controllers or microcontrollers can be implemented in single or multi-core configurations, and can be standalone devices or integrated within other system components. They can be coupled to memory, storage devices, other input/output devices, or networks for the exchange of data or instructions. They can be part of an embedded system, and can be designed for low power consumption, robustness, fast processing capability, or other design considerations as needed for their intended use. Furthermore, they can support various software platforms or operating systems, can be programmable using various programming languages, and can be updated or reprogrammed as needed to add functionality or to correct errors.

The various illustrative logical blocks and modules described in connection with the embodiments disclosed herein can be implemented or performed by a machine, such as a general purpose processor, a digital signal processor (DSP), an application specific integrated circuit (ASIC), a field programmable gate array (FPGA) or other programmable logic devices. These can include processors on a mobile device such as a smartphone, or a processor within a cloud-based computing system. These can be discrete gate or transistor logic, discrete hardware components, or any combination thereof designed to perform the functions described herein. A general purpose processor can be a microprocessor, but in the alternative, the processor can be a controller, microcontroller, or state machine, combinations of the same, or the like. A processor can also be implemented as a combination of computing devices, e.g., a combination of a DSP and a microprocessor, a plurality of microprocessors, one or more microprocessors in conjunction with a DSP core, or any other such configuration.

The steps of a method, process, or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, SSD, or any other form of computer-readable medium known in the art, including cloud-based storage systems. An exemplary computer-readable medium can be coupled to the processor such that the processor can read information from, and write information to, the memory/storage medium. In the alternative, the medium can be integral to the processor. The processor and the medium can reside in an ASIC. The ASIC can reside in a user terminal which could include but is not limited to devices like a computer, smartphone, tablet, or dedicated medical device. In the alternative, the processor and the medium can reside as discrete components in a user terminal. The implementation may also be configured for distributed computing environments where tasks are performed by remote processing devices linked through a communications network.

In one or more embodiments, the control module can be miniaturized, and the respective components adapted to a case design that enshrouds a pump, with support for an external sensor connection including but not limited to gold pogo pin connections, a cable connection, a radio frequency connection, etc. In yet another embodiment, the box can be scaled up and used in conjunction with a non-ambulatory pump in a hospital, home, or field setting to track the status of medication delivery including but not limited to chemotherapy, immunotherapy, Parkinson's, intravenous infusions/injections, intradermal injection, intraocular infusion/injections, intracranial infusion/injections, etc.

In yet another embodiment, the control module can be used in conjunction with a manual injection device including, but not limited to, a smart insulin injection pen, an EpiPen, a needle and syringe, an autoinjector, a smart autoinjector, or the like wherein the box can connect to a sensor in the device housing or connected inline to the flow path or reservoir to track the quality and status of the medication being administered.

In yet another embodiment, the control module can be configured to accept data from non-connected sensors via a wireless communication protocol, which may include but are not limited to a continuous glucose sensor, a heart rate monitor, a smart watch with sensors, and the like. Furthermore, the control module may be configured to operate with an external device such as a smartphone and transmit all the data or parts of the data collected to the device for data processing and storage.

A control module including a data collection box as described above may allow for ambulatory data collection and support the deployment of a machine learning model also as disclosed herein. The following disclosure may elaborate further on how the deployment of such a model with a data collection device may be possible, for example via a collection of algorithms and models capable of monitoring the infusion status in real-time and relaying the quality of the infusion to the user. A system as disclosed herein may be specifically designed for infusion failure detection, and/or further extended as a general-purpose infusion monitoring system. In one embodiment, a model as described above may be paired with user inputs and a log of historical events and infusions to generate a personalized assessment of the infusion site for the specific user. This set of inputs may be tracked, logged, and analyzed on an external device in communication with the pump or as a standalone system where the data from the pump is uploaded. In one embodiment, a system as disclosed herein may comprise a standalone software platform that can be adapted to fit an array of use cases ranging from infusion monitoring form a nurses' station in a hospital setting, a remote patient monitoring tool for patient receiving infusions in a site remote to where the data is being processed, as a monitoring tool for parents/loved ones of a person using an ambulatory or stationary infusion pump which has access to the data from the cloud, and the like.

In another embodiment, the control module can be integrated with a wearable device such as a smartwatch or a fitness tracker, that is capable of monitoring the user's physiological parameters in real time. The monitored data can be used in conjunction with the infusion status to provide a more comprehensive understanding of the user's health during the infusion process. This integration can provide more personalized care, for instance by modifying the infusion rate based on the user's physiological response.

In yet another embodiment, the control module can interface with environmental sensors, including temperature, humidity, and air quality sensors, among others. These sensors can provide additional context for analyzing the effectiveness and safety of medication delivery, particularly in the case of sensitive medications or user environments.

An additional embodiment can involve the control module incorporating an artificial intelligence (AI) module, capable of learning the user's patterns and preferences, and predicting potential problems. This AI can provide proactive alerts or recommendations, enhancing the safety and effectiveness of the medication delivery process.

In another embodiment, the control module can be used in telemedicine scenarios, allowing remote healthcare professionals to monitor the medication delivery process, and provide instructions or interventions as needed. This can be particularly useful in remote or rural areas, or in situations where the user has mobility issues.

In yet another embodiment, the control module could include an emergency alert system which can be triggered under critical conditions. The alert system can send emergency notifications to predefined contacts such as caregivers, family members, or healthcare providers.

In another embodiment, the control module could work in concert with smart home systems, integrating infusion monitoring with a broader network of devices and sensors for holistic health monitoring and management.

Referring again to FIG. 17, a model implementation stage 120 of the method 100 may be provided with respect to a current subject 121 and include the collection of time series data 122 and determining of relevant fluid delivery characteristics 123 in a manner as described above, further wherein one or more previously generated models are selected 124 and for example deployed in a cloud environment and accessible from an external device in communication with a system which is logging data related to the infusion. In an embodiment, a control module as described above may be used as the data acquisition device logging data from sensors placed in-line with the pump, sensors located inside the pump, or external sensors in communication with the pump or other device including but not limited to a medication delivery pen, and is in communication with a smartphone application, which visualizes the data in a user-friendly interface and provides real-time alerts in case of abnormalities. The smartphone application can access an application program interface (API) hosted on a cloud provider, ensuring seamless integration with the cloud-deployed models and enabling the application to leverage their predictive capabilities.

In an embodiment, the system may comprise a foundational algorithm which receives information from the current subject's insulin pump regarding delivery timings (start, stop) based on the hardware delivery mechanism (pressure driven flow, plunger driven flow, electro porous flow, etc.) to establish the start of and perform a precise time series analysis of medication delivery from the pump to the subject. Once the delivery has started, the algorithm may use this start of delivery and parameters regarding the pumping mechanism and correlate those to a specific pressure value based on hardware mechanism (actual actuation of the pump to create fluid flow), flow conditions (rate and volume), and time (start time of actuation, final time of actuation). This data is sent from the pump to an external device including but not limited to a smartphone, a smart watch, a configured data received, a connected device such as a computer, laptop, or tablet, or any other device configured to accept data from a secondary device via a wired or wireless connection. The start of the infusion is used as an event indicator and the data is sent to the cloud via an API endpoint, where a function creates a new database entry and sends the connected device an identifier for accessing this entry. Once the infusion has started, if needed, the algorithm can increase the sampling rate of the sensor being used to track pressure, flow, or other parameters related to the medication delivery. As the data is received, the device connected to the API may continuously send the data to be aggregated in the database and marked for example as "infusionRegion" while the pump is actively infusing. Once the pump stops, the algorithm continues to sample the data until some determined time interval based on the initial infusion. The estimation of this time interval post infusion may be calculated by using the following:

$$\frac{\text{Target Volume Infused } [ul]}{\text{Infusion Rate } [ul/\text{min}]} * \frac{1\ [\text{min}]}{60\ [s]} * C = \text{Time Interval to wait post infusion}$$

In this example, the target volume is the desired medication infused, infusion rate is the infusion rate used by the pump for the programmed infusion, 1/60 is a time conversion factor, and C is some constant which can be predetermined and tuned based on the infusion rate, infusion size, or other factors by the manufacturer or algorithm During the output time interval to wait for post infusion the algorithm will continue to collect data for that infusion after the pump has stopped delivering the infusion.

Figure 24:
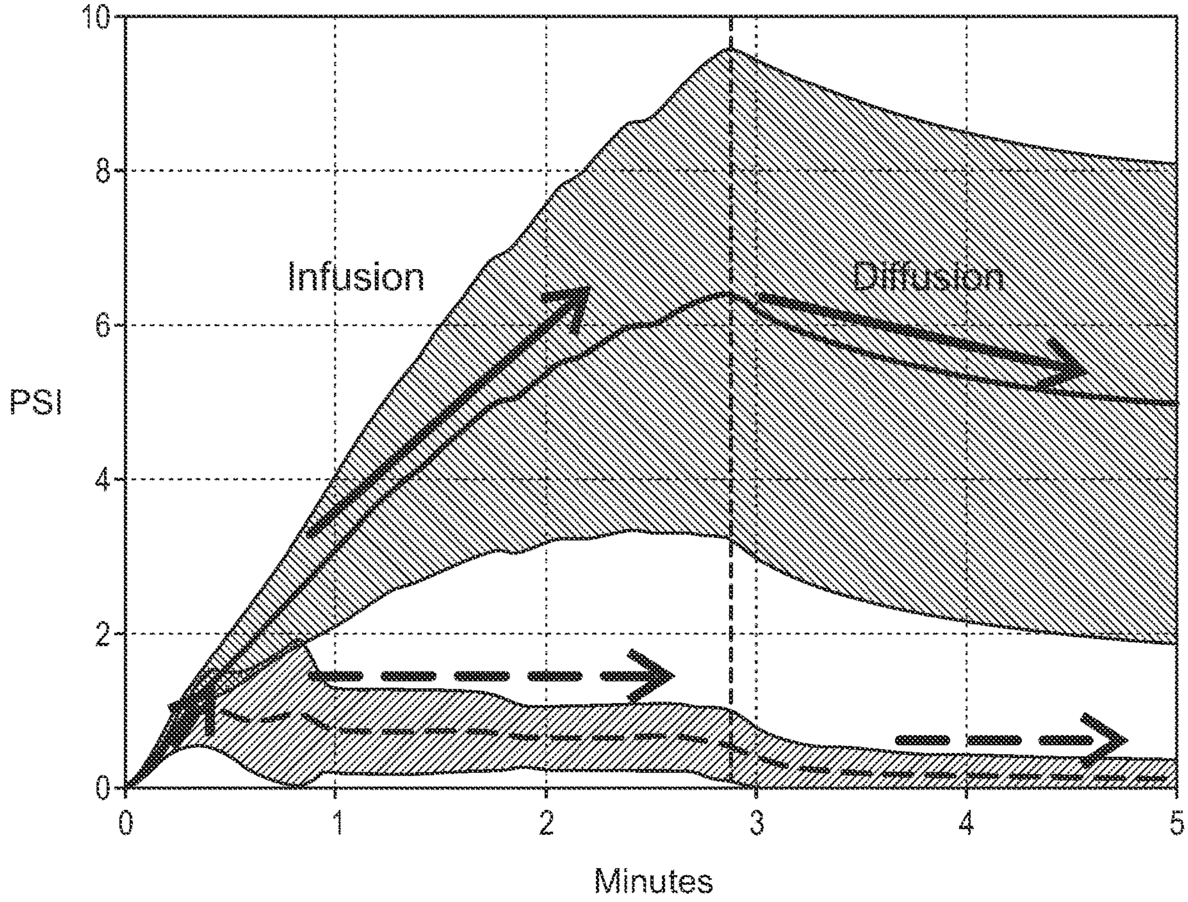
FIG. 24 is a graphical diagram representing an exemplary active infusion area and post-infusion area for each of a normal infusion and a malfunction.

The data collected during this period may be logged as "diffusionRegion" and saved in the same location as the "infusionRegion" data in the cloud. Both infusion and diffusion regions in a pressure tracing may be as illustrated in FIG. 24, with a noticeable difference between a successful infusion (smaller tracing) and a failed infusion (large tracing).

Once logging is complete, the device connects to the API where a first function accesses the data stored in the database using the ID originally provided, processes the data, and extracts relevant features (fluid delivery characteristics) from both infusion regions and a combination of both regions. The features may include but are not limited to maximum pressure, area under the curve, standard deviation, skewness, quartile values, and the like. This process data may then be passed to a second function which imports a created model and scalar from a storage location, applies the model to the inputs, and returns a fluid delivery state (label) for the infusion such as normal, partial occlusion, full occlusion, leak, dislodgement or other. The aggregated data and features are stored, and the label sent back to the connected device for the user to see and interpret. The model may be a machine learning model such as a support vector machine, random forest, logistics regression model, neural network, or other model which leverages calculated features from the tracked dynamic including flow, pressure, or the like.

In various embodiments, the data as described above may be aggregated on the connected device before being sent to the server, and/or may be stored, processed, and analyzed on the connected device without the need for a server. The data may be combined with other sensor data and a different model may be used to estimate the infusion label. The data may never be sent to a connected device and instead stored, processed, and analyzed on the pump. In another embodiment, the processing may be done as the data is being collected and not at the end, or the fluid delivery state and fluid delivery characteristic(s) both sent to the user rather than just the state (label).

In one embodiment, the system can be configured to communicate with various Internet of Things (IoT) enabled devices. For instance, the system could interact with a smart home system or an assisted living system, which may react based on the infusion status. A signal, message, or alert could be sent to these IoT devices upon the detection of an infusion failure. This signal could initiate a set of predefined actions such as sounding an alarm, sending a notification to a caregiver's mobile device, or alerting a remote monitoring station, thereby facilitating immediate response to any infusion issues. The system may also be designed for use in remote patient monitoring scenarios. In such cases, data related to the medication delivery may be transmitted over the internet or other communication networks to a remote monitoring station, where healthcare professionals, caretakers, parents, or caregivers can monitor and analyze the patient's infusion status in real-time, thus enabling healthcare delivery even in remote or inaccessible locations.

In another embodiment, the system may use predictive analytics to anticipate future infusion failures. The machine learning model might be trained on historical data to identify patterns or signs leading up to a failure. By using these predictive capabilities, the system could provide early warnings about potential infusion issues before they occur, enabling preemptive interventions and minimizing risks to the patient.

In yet another embodiment, the system may be integrated with Electronic Health Records (EHR) systems. Upon completion of each infusion or at regular intervals, the system could automatically update the patient's EHR with relevant infusion data. This would reduce manual data entry, increase the accuracy of records, and ensure that healthcare providers have the most recent and accurate data about the patient's medication infusion history.

The system could also be adapted for multi-patient monitoring in a hospital or care home setting. In this embodiment, a single control module or monitoring station may be configured to communicate with multiple infusion pumps simultaneously. Each pump could transmit its data to the control module, which could then analyze the data and track the status of each patient's medication delivery. This would facilitate efficient monitoring and management of multiple patients by a single healthcare provider.

Figure 25:
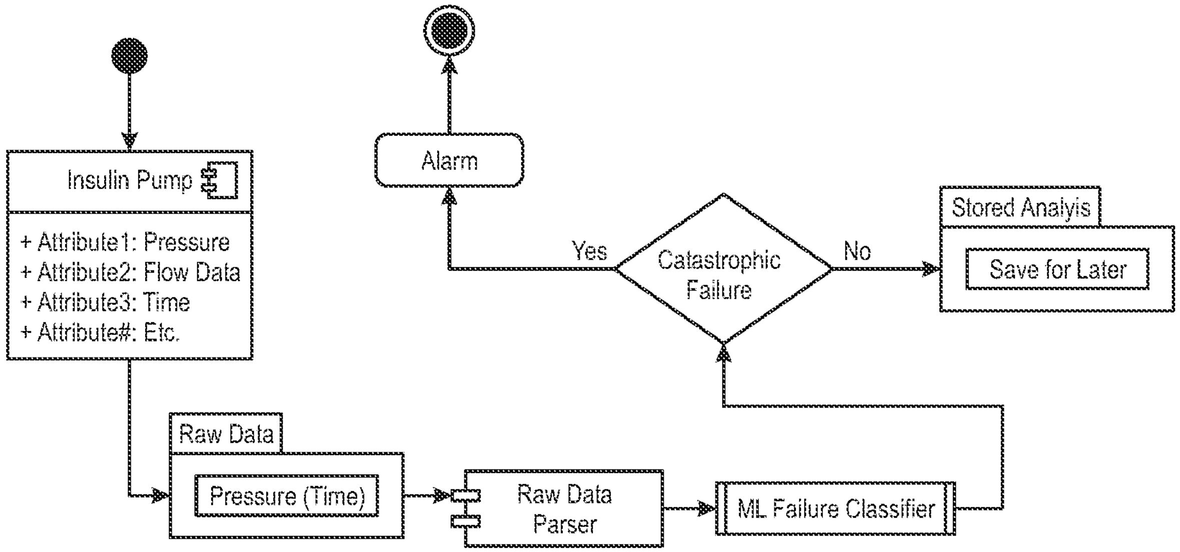
FIG. 25 is a block diagram representing an exemplary model comprising an algorithm to sound an alarm if a failure is detected.

In an embodiment the determined fluid delivery state can be used to decide whether to send an alert, sound an alarm, or store the data, as illustrated for example in FIG. 25.

In another embodiment, data may be collected and processed on the pump, and sent to a connected device over a wireless protocol, wherein that device sends the data to a server where the data is viewable on a web application.

Algorithms as conventionally deployed on insulin pump systems may rely on blood glucose sensing to provide insight into a difference between the target blood glucose and the current blood glucose level, essentially creating a feedback system which aims to minimize the error between the target and the current level. While many such systems have been shown to be successful at maintaining users within an acceptable range, many disturbances can impact the system's ability to maintain the user within an acceptable blood glucose range. External disturbances such as variance in tissue health at the chosen infusion site can alter medication absorption rate by the site, wherein a delay in time to affect or a change in the physiology of the site can impact the sensitivity to the medication through that site, resulting in an increased or decreased need for medication. Infusion set failures can result in the medication never reaching the user's blood stream, or there can be a leak at the site meaning the fluid has exited the system and will never be absorbed. Environmental variables such as a user's pet eating an infusion set tubing can result in medication never reaching the user. The user being sick can temporarily increase or decrease the need for medication throughout the course of the sickness. The user being on their menstrual cycle can result in excess hormone production which impacts control, or the user suffering from other diseases can impact the actual blood glucose levels of the user. These external disturbances, while detrimental to a system's ability to maintain control, are sometimes unmeasurable by blood glucose alone because of the many confounding factors that can impact blood glucose meaning that the algorithm cannot accurately differentiate a blood glucose impact from an insulin infusion or an external event.

To address these problems in conventional systems and methods, a failure detection system as disclosed herein actively accounts for unexpected events and disturbances.

For example, in one embodiment a system according to the present disclosure can monitor a medication delivery as a 10 uL infusion is being administered, actively sample the data, and determine that the infusion has been successful, meaning that the medication was delivered to the infusion site. The system can relay that information to the control algorithm, wherein the confidence in a predicted future blood glucose can be increased. If the blood sugar levels are not responding as anticipated, an external disturbance event (e.g., an unannounced meal) can be estimated.

In another embodiment, the system detects a successful infusion, but the user's blood sugar is not decreasing fast enough, so a more aggressive medication delivery schedule can be selected without fear of under-dosing.

In another embodiment, the system detects a failure in the delivery system and prompts the user via a notification or alert, at the same time providing the control algorithm with an estimated delivery efficacy score which it can use to determine the amount of medication it needs to administer to overcome for the lower efficacy until the user can change the infusion site. Alternatively, the control algorithm can choose to stop all fluid delivery, if for example the goal of the system is to reduce unnecessary medication consumption in the event of an efficiency score less than x %.

The described system may accordingly be distinguished from conventional techniques. For example, a conventional algorithm may include the target blood glucose (BG) level as a target input and continuous glucose monitor data as a current value, leading to an error which can be estimated as:

$$\text{Target BG} - \text{CGM Data} = \text{error}$$

$$G_{insulin\ needed}(\text{error}) - \text{insulin on board} = \text{insulin needed}$$

The error can then be used as an input by the control algorithm or user to calculate the insulin requirement, G(error), after accounting for the insulin on board (insulin already delivered). The output (insulin needed) tells the user to deliver or wait until it is consumed, assuming an excess has been delivered. After the delivery and effect of the disturbance, the new blood glucose level (blood sugar) is an output which serves as a feedback stream to the system as the new CGM Data input.

$$\text{disturbances} + \text{blood sugar} = \text{CGM Data}$$

In a system using conventional algorithms, a correction factor associated with the disturbance cannot be accurately estimated or accounted for outside of the new error term, at least partially due to the system not knowing if the medication was even delivered.

In a system according to the present disclosure, medication delivery may be tracked and a determination made as to whether the fluid delivery was successful, and if the fluid delivery is unsuccessful it can estimate the fluid (e.g., insulin) delivered by analyzing the pressure waveform and estimating a fluid delivery amount utilizing a transfer function and add to the error calculation in the form of a correction factor (e.g., step 125 in method 100) which would help the system account for any disturbances to the system.

$$G_{insulin\ requirement}(\text{error}) - \text{insulin on board} + \text{correlation factor} = \text{insulin needed}$$

The correction factor in this embodiment would contribute to the total insulin needed, whether it is because the insulin never reached the user, the insulin need is greater than previously thought, less insulin is actually needed due to a change in the user, or the like. The system may accordingly provide the benefit of serving as a feedback based on the quality of the infusion on an administered infusion, and can act as a feedforward system by helping to correctly estimate the future insulin needs of a user based on changing site characteristics.

In one embodiment, the system's response to the determined fluid delivery state can be customized according to user preferences or patient's clinical needs. This may involve the creation of multi-modal alerts, wherein the system could generate visual, auditory, and tactile alerts. For example, a visual alert could involve flashing a specific color or pattern on a connected device, an auditory alert could be a unique sound or series of beeps, and a tactile alert might take the form of vibration patterns on a wearable device. Such a system may offer enhanced accessibility for users with different sensory abilities.

In another embodiment, the system can integrate with other health-monitoring systems or wearable devices. This could allow the data collected and processed on the pump to be used in conjunction with other health metrics like heart rate, body temperature, sleep patterns, and physical activity levels. Such a comprehensive health-monitoring system could provide a more holistic view of the patient's health and potentially identify correlations between these metrics and infusion success or failure.

In yet another embodiment, a user-friendly interface can be developed for the web application where the data is viewable. This interface can incorporate visualizations of the infusion data, provide detailed explanations of the infusion states, and offer recommendations for actions to take based on the fluid delivery state. The interface could be designed to be easy to navigate for users of various ages and levels of technical proficiency, thus making the system more accessible to a wider range of users. Furthermore, the system can be designed with advanced disturbance-detection capabilities. For instance, it can learn from historical data to recognize unusual patterns or anomalies that could indicate disturbances like variance in tissue health, infusion set failures, or changes in the user's physiological condition. Machine learning techniques such as anomaly detection and pattern recognition could be employed to enhance the system's ability to detect and respond to these disturbances. In addition to recognizing these disturbances, the system could also be designed to automatically adapt its control strategies in response to these disturbances. This could involve adjusting the infusion rate or volume, altering the schedule of infusions, or suggesting alternative infusion sites to the user. Such adaptive control strategies could help maintain optimal blood glucose levels even in the face of varying external disturbances.

One skilled in the art can see how this infusion-based system can be applied to another type of medication delivery system where instead of insulin, Parkinson's medication is being administered and the quality of the infusion can be used to know if the medication is not being administered within the desired time interval and can have negative impact on the therapy. Similarly, this can be applied to any fluid delivery system such as liquid feed being administered to infants in the neonatal intensive care unit, or intravenous infusion being administered across multiple pumps and the needle is removed accidentally or becomes infiltrated and the site is compromised. The system could for example alert a person responsible for monitoring the delivery and prompt them with actionable information via a wireless notification system, alert/alarm, text message, phone call, prompt on a computer program, etc. (e.g., step 127 in method 100), and/or generate output signals such as control signals for regulating one or more actuators associated with fluid delivery (e.g., step 128 in method 100).

In another embodiment, a system as disclosed herein may aggregate all infusion quality data and create a map of infusion sites with the highest number of successful or failed infusions. The system may further recommend a site to be used based on historical performance, for example relative to a particular subject and/or an aggregate population of subjects. This map may for example be visualized on a mobile phone, computer program, web-based application, mobile application, relayed via a text message, voice call, or other form.

In one embodiment, the system may employ machine learning algorithms, such as reinforcement learning, to continuously learn from the aggregated infusion quality data and dynamically adjust its site recommendations based on these learnings. This could involve tracking the success rates of infusions at different sites and assigning scores or probabilities to each site. The system could then recommend the site with the highest score or probability for the next infusion. This approach could improve the chances of successful infusions and potentially reduce the risk of complications associated with infusion failures.

In another embodiment, the system could take into account the physical characteristics and medical history of individual subjects when recommending infusion sites. For example, it could consider factors like skin condition, fat distribution, previous site reactions, and the presence of any underlying conditions that might affect the absorption of the medication at different sites. By tailoring its recommendations to each subject's unique characteristics, the system could offer a more personalized and effective approach to infusion site selection.

In yet another embodiment, the system could incorporate predictive analytics to forecast the likelihood of successful infusions at different sites in the future. This could be based on historical performance data, as well as trends and patterns identified from the aggregate population of subjects. Such predictive capabilities could help subjects and healthcare providers plan infusion schedules and strategies in advance, thereby enhancing the overall management of the medication delivery process.

Regarding visualization, in one embodiment, the system could present the site map in a 3D model form, allowing users to interactively explore different sites and view detailed information about their performance. This could be implemented using augmented reality (AR) or virtual reality (VR) technologies, which could provide a more immersive and intuitive way for users to understand the data. In another embodiment, the system could offer a time-lapse feature that allows users to see how the performance of different sites has changed over time. This could be represented visually through changes in color, size, or shape of the sites on the map. Such a feature could provide valuable insights into the long-term trends and variability in infusion success rates at different sites.

Figure 26A:
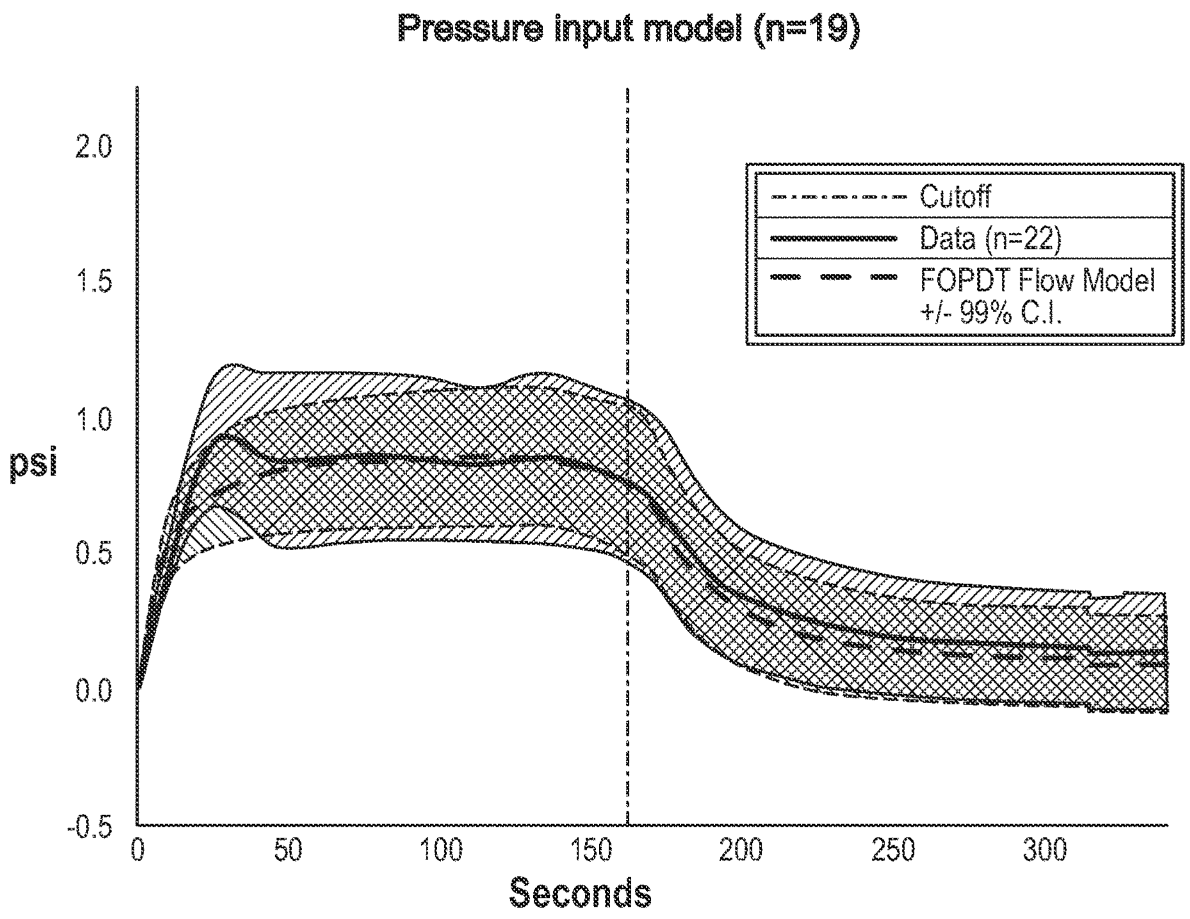
FIGS. 26A to 26C are graphical diagrams representing, respectively, an exemplary filtered pressure input waveform, an exemplary flow rate waveform, and an exemplary volume waveform as estimated from flow rate.
Figure 26B:
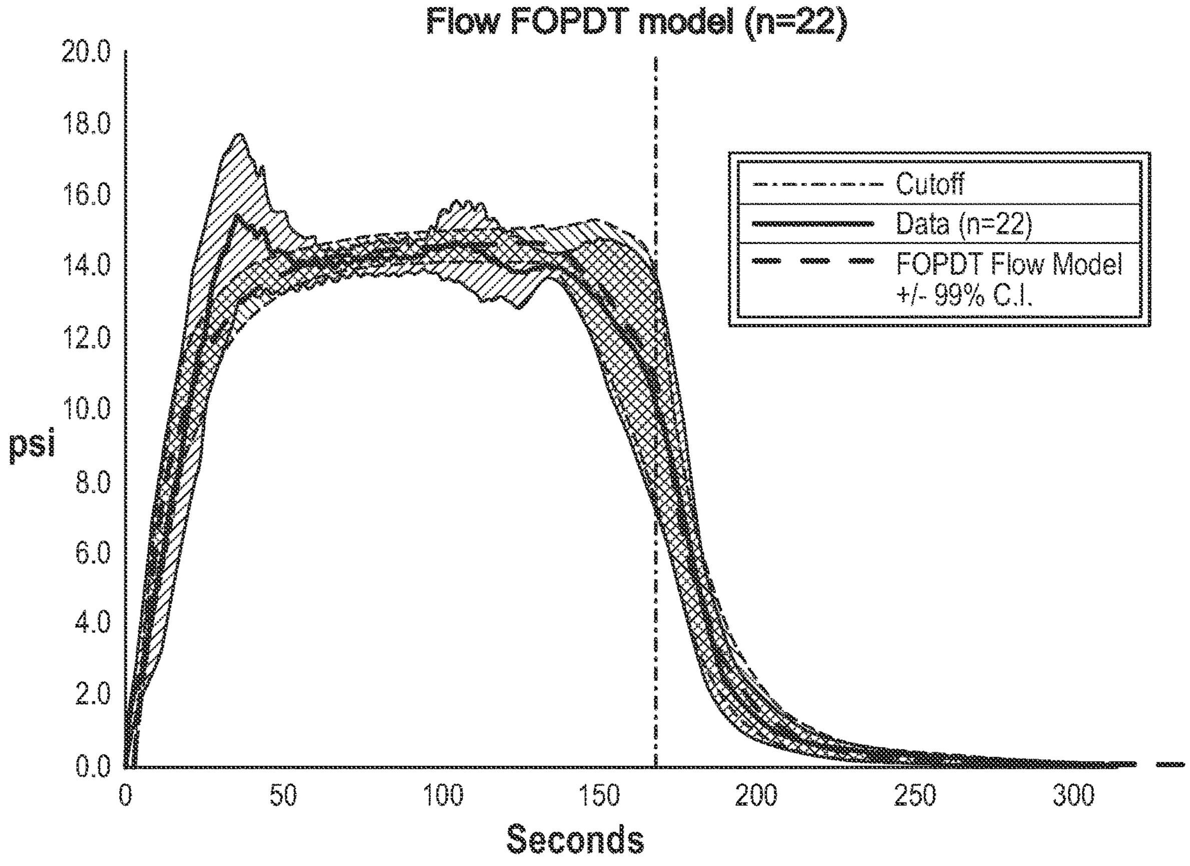
Figure 26C:
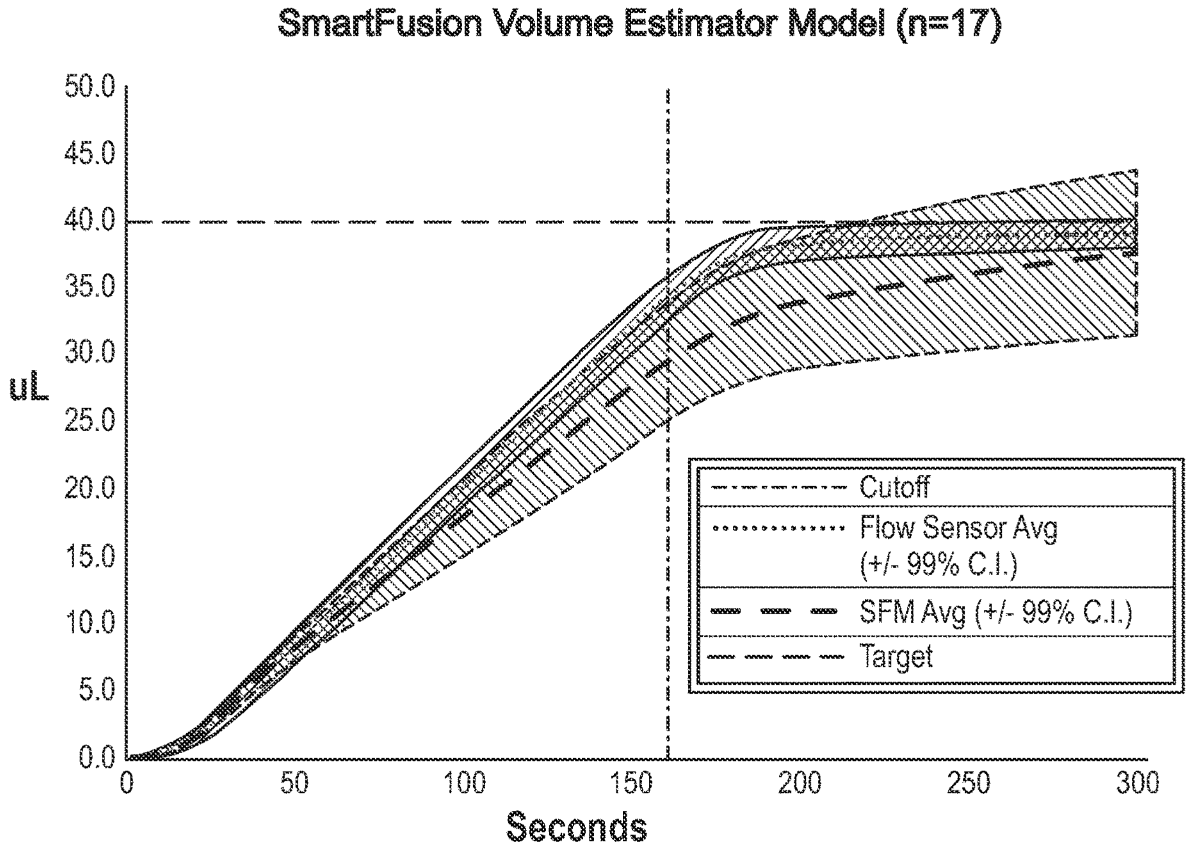

In another embodiment, a system as disclosed herein may be configured to display a live estimation of infusion performance (efficiency) based on pressure data or other infusion-related performance data including but not limited to force data, impedance data, or motor current data, which is then transformed into fluid flow data and the area under the curve of that flow rate estimates the volume delivered during the infusion, for example as illustrated in FIGS. 26A to 26C, wherein FIG. 26A illustrates an exemplary filtered pressure waveform, FIG. 26B illustrates an exemplary flow rate waveform as estimated from filtered pressure, and FIG. 26C illustrates an exemplary volume waveform as estimated from estimated flow rate. This process can be accomplished by creating a transfer function from pressure to flow based on experimental data collected, as previously described. Furthermore, this information may be related to the user or interested party as a percentage indicative of site efficiency where the efficiency of any site may at any given time, t, can be calculated as the estimated volume delivered at time, divided by the expected volume delivered at that same time multiplied by 100%.

$$\text{efficiency }(t) = \frac{\text{actual }(t)}{\text{expected }(t)} * 100\%$$

The efficacy of fluid infusion may in an embodiment be visualized via a gauge chart, for example using the color red to indicate a failed infusion and the color green to indicate a successful (normal) infusion. This data may be visualized on a mobile device, web application, computer program, secondary device operated by someone not including the user of the pump. The system might also provide more detailed visual representations of infusion performance. For example, in one embodiment, it could display a time-series chart showing the changes in infusion performance over time, which could help users and healthcare providers identify trends or patterns. In yet another embodiment, the system could include a feature that allows users to compare the performance of different infusions side by side. This could help them identify any deviations from the norm and potentially reveal correlations between infusion performance and other factors, such as the time of day, user's activity level, or specific infusion sites. Regarding user alerts, the system could be designed to provide customized alerts based on the user's preferences or specific requirements. For instance, in one embodiment, the system could send alerts to the user's mobile device, smartwatch, or email when the estimated infusion efficiency drops below a certain threshold. It could also alert healthcare providers or caregivers in case of significant or repeated infusion failures In an embodiment, a system as disclosed herein may be in communication with the pump's algorithm which can provide additional details for analysis such as a notification when the pump's reservoir has changed its level of medication (2 mL, 3 mL, etc.) in addition to any registered changes (changing infusion site, etc.). However, these actions may be logged on a separate device such as a personal diabetes/disease manager or smart phone/smart device. The pump may also inform the system of any native errors it has identified, including but not limited to a low battery state, mechanical failure of the system, inability to deliver medication, or any other relevant alert such as voltage inconsistencies for internal components or a change of state such as charging mode. The pump may also let the system know of any parameters relevant to the infusion system, such as the type of infusion set. The algorithm may examine the blood glucose reading from the external monitor and predict what a future blood glucose could be based on a trained algorithm, wherein the insulin pump's delivery configuration is factored in, along for example with delivery history, to estimate future impact on blood glucose based on current insulin on board, previous patient history, and possible future insulin needs based on future logic considerations if the patient's future blood glucose result in a large difference between predicted, actual, and estimated response. This feature may allow for the algorithm to operate without the need for a physical CGM or BG measuring device, and rely primarily on the predicted BG values and other parameters.

In an embodiment, a control algorithm as disclosed herein, in addition to factoring the previously mentioned variables, may also consider any available in-line fluid pressure or other such input from a sensor or calculated pressure value. During infusion the system may consider the in-line fluid pressure as a metric for evaluating tissue response based on a time series analysis or other type of analysis of the pressure curve. The pressure readings may be considered as a unified subset comprising equipment, environmental, and physiological response to medication infusion and normal use of the technology. For example, the output pressure value may be 1.7 psi, wherein: 0.5 psi is attributed to the pumping mechanism; 0.2 psi is attributed to the response from the medical tubing, cannula contracting, dilating due to medication flow, environmental conditions, or wear and tear from normal use; 0.6 psi may be attributed to large movement from the patient, environmental conditions (high heat, high elevation, etc.), and external factors such as white noise or indiscernible unaccountable factors; and 0.4 psi may be attributed to the physiological tissue response. The system may be trained to account for these different factors and able to assess infusion conditions and infusion site response.

The calculated response may be compared to a predicted response including, but not limited to, the patient's infusion history, trained data during the creation of the algorithm, new data models created from or adapted from other patients who utilize this technology, or other new forms of data types later introduced. By analyzing the pressure waveform, the CGM readings, pump actions/commands, in combination with machine learning/data science principles, the algorithm will be able to assess whether the medication amount registered by the pump for delivery is equivalent to the medication received by the patient.

By considering some or all of the principals described above, the algorithm may be able to discern between an infusion site which is receiving all the medication being infused by the pump and how long it takes to settle into the patient either via absorption into the tissue, the blood stream, or any other method which results in the medication entering the patient's body. If the system detects a discrepancy between the amount infused by the pump and the amount introduced into the body, it may use the pressure signal to distinguish a failed infusion of medication, missed infusion response (some medication reaches the patient, some may not), a delayed infusion response (insulin is delivered from the pump, the pressure response showcases medication being delivered and received, but there is a longer than expected period of absorption), a complete lack of medication delivered either during infusion or later (block of infusion, leak from the site resulting in no medication staying in the patient, or medication that is in the line and enters the patient later than expected), and any other form exclusive of a "successful" infusion classification.

The pressure signal from an external pressure sensor located anywhere in the infusion path, by the pump, at the site, implanted in the tissue, internal to the pump, or externally mounted on a separate device such as a combined CGM and infusion set, or any other device with a pressure/force sensor may be used in additional ways than the ones described above. For example, the pressure signal may be used as a method of evaluating patient activity levels. Pressure readings are easily influenced by a number of things such as elevation, viscosity of the fluid, environmental factors, and others. Because of this, the system may be able to use these pressure abnormalities/anomalies/disturbances (changes from expected performance/signal to noise ratio) to estimate changes in infusion conditions.

A system as disclosed herein may utilize a number of methods to correlate pressure signal disturbances to any number of changed infusion states, both related to the patient or otherwise. The pressure signal for example may have unique identifiers or attributes which may be associated with a patient going from a sitting position to a standing position, or from a normal activity position to a more active movement (working out, jogging, etc.). These measurable changes in the pressure waveform may be analyzed based on information from external devices (CGM, heart rate monitor, SPO2, etc.) and infusion devices such as an externally worn pump or implantable pump.

The algorithm may see an increased activity identified by the increase or disturbance of the pressure signal and check with the CGM to see if blood glucose is being affected based on known physiological responses to blood glucose based on patient activity. The algorithm may also look at the insulin pump to see if delivery conditions have changed or if there have been any changes in the system either initiated by a control algorithm or patient. If there is no change in the system, then the increase in pressure signal disturbance may be attributed to external factors.

Additionally, the system may be trained on different events, such as increased heart rate or increased level of activity, and correlate certain pressure curves/responses to a change in activity (sedentary to active) or an increase in blood flow (higher heart rate, or increased blood flow to a specific area for whatever reason [sleeping on your arm and rolling over releasing pressure on the site]). The system may also be able to use these different variables to make predictions regarding patient state, such as for example eating, exercising, stress levels, etc. By training the system on waveform analysis using other devices, the system may allow for estimating any changes in state without the need for these external devices.

Conversely, the algorithm may use other sensors which the patient may choose to pair with the system for increased performance and considerations such as an accelerometer from their smartphone or a heart rate sensor from a smart device, to supplement its own interpretation of environmental factors or in conjunction with the readily available devices. This feature will allow for a modular algorithm where some patients may choose to pair additional devices and relay that information to the algorithm, or they may choose to limit data sharing between devices. All of these considerations may be altered based on unique values from the patient or historical patient data allowing for tighter parameters or looser parameters based on either an updated model, personalized performance metrics based on patient feedback and interaction with the device, or the like. The modularity of the system may allow for a reduction of physical devices by the estimation of certain parameters such as blood glucose from insulin pump data, meal logging, and exercise data, or estimating meal information from habit analysis, blood glucose data, insulin pump data, and exercise data. To actualize this modular algorithm the minimum requirements may for example include an insulin pump, pressure analysis software, and a CGM or enough supplemental data streams to estimate blood glucose (exercise, meal logging, heart rate, SPO2, etc.).

In one embodiment, the system could include an adaptive machine learning model, trained to predict the value of a data stream from an unpaired device using historical data and data from other paired devices. This "synthetic" data stream could be used to estimate key parameters in the absence of direct measurements, effectively expanding the capabilities of the system without requiring additional hardware. For example, the model could predict blood glucose levels based on insulin pump data, meal logs, and exercise data, allowing users to estimate their blood glucose levels even when they don't have a CGM paired with the system.

In another embodiment, the modular algorithm could be capable of integrating data from a variety of sources, such as wearable devices, smartphone sensors, or even external databases like weather information or air quality indexes. The algorithm could use this information to account for a wide range of environmental factors that could affect blood glucose levels, such as physical activity, stress levels, sleep patterns, or climate conditions. This could further enhance the accuracy of the algorithm's predictions and its ability to adapt to individual users.

The system could also implement advanced data fusion techniques to combine information from different devices or sensors. For example, in one embodiment, it could apply sensor fusion algorithms to create a more accurate and reliable "synthetic" data stream, leveraging the strengths of each individual sensor while mitigating their weaknesses. In yet another embodiment, the modular algorithm could include a feature that allows users to manually input data that might not be captured by their paired devices. For example, they could log their meals, record their mood, or note any unusual events, such as illnesses or changes in their routine. The algorithm could use this manually entered data to refine its predictions and provide more personalized recommendations.

In terms of user interface, the system could be designed to display the "synthetic" data stream alongside the actual data streams from the paired devices, allowing users to compare the predicted values with the measured values. This could help users understand the algorithm's performance and build trust in its predictions. As the algorithm learns from historical data and user feedback, it might also update its predictions and recommendations over time. In an embodiment, the system could include a feedback mechanism that allows users to rate the accuracy of the "synthetic" data stream and provide input that could be used to improve the algorithm's performance. Finally, the system might include safeguards to ensure that the "synthetic" data stream is used responsibly. For instance, in an embodiment, it could include a feature that alerts users when the predicted values are significantly different from the measured values, indicating that the "synthetic" data may not be reliable. It could also provide warnings or disclaimers informing users that the "synthetic" data stream is only an estimate and should not replace direct measurements, particularly in critical situations.

Various features as disclosed herein may benefit from a system that has an externally mounted pressure sensor system with an orthogonal flow path to a sensor which flows into a chamber where in-line fluid pressure is able to be read. To support this externally mounted system, a retrofitted device or enclosure may be mounted onto a pump which is capable of ambulatory medication delivery or is stationed near the patient, a standalone pump, a pump which is part of a large set of infusion pumps, pumps designed for intravenous infusion, pumps designed for non-ambulatory use, and pumps designed for at home or hospital use. A pump that is implanted into the patient may also be considered, where an external monitor is mounted adjacent to the implanted pump and can interact with the pump via a method of non-direct communication (Bluetooth, Wi-Fi, near field radio frequency, or other form of communication) which may allow for a system to collect information from the pump.

In an embodiment the system will rely on a clear signal interpretation from a sensor. The system may be internal to the insulin pump or external mounted somewhere along the fluid path or as an external sensor spliced into the infusion path.

In an embodiment, associations may be investigated between infusion site selection, wear habits, and patient involvement in therapy and its impact on system performance. For example, an algorithm according to the present disclosure may be able to better classify performance of a pump based on infusion site selection. For this the system will require the patient to provide input relating to the infusion site, natively by the software based on a calibration period where a baseline pressure value is established and correlated to a higher elevation between to the pump and the site signifying use in the abdomen or other, whereas a lower baseline pressure may indicate a lower infusion site from the pump reference such as a thigh or other. The system may also ask the patient to enter the site via a GUI on their designated smartphone or external device which they pair with their pump. This selection may also occur on the pump itself. With the site logged, the algorithm may be able to consider/build different profiles based on the characteristic tissue at the site and its specific response (e.g., the abdomen always has x response features, lower back has y), and this established assessment and history may assist in comparing the current wear period with a previous wear period from the same site or from a different site. This may benefit the patient because they may see a difference in therapy performance due to a physiological difference in site or a recent change in hardware such as a pump upgrade, infusion set type change, or change in activity. This historical comparison may be categorized by the system and presented to a physician for further evaluation which may assist in changing therapy recommendations for the patient or compare previous hardware combinations.

In one embodiment, the system could include a site selection and mapping feature, designed to help patients select the optimal infusion site and track the performance of different sites over time. This feature could be integrated into a mobile application or a web-based platform, which the patients can access through their smartphones, tablets, or computers. In another embodiment, the system could incorporate a graphical user interface (GUI) that displays a map of the patient's body, allowing them to visually select the infusion site. This could involve a 3D rendering or a 2D illustration of the human body with different areas selectable based on appropriateness for infusion, including the abdomen, thigh, lower back, and others. As the patient selects a site, the GUI could provide real-time feedback, for example, by highlighting the selected area or displaying additional information about the site. For each site, the algorithm could create and store a profile that includes the characteristic tissue response, the historical performance of the pump at that site, and any other relevant information. The profile could be continuously updated as the system collects more data, providing an increasingly accurate representation of the site's characteristics. In addition to the patient's input, this profile could incorporate data from various sources, including the insulin pump, additional paired devices, and possibly even external databases with aggregated data from other patients.

In another embodiment, the system could include a site rotation feature that helps the patient choose new infusion sites over time. The feature could use an algorithm to suggest the most suitable sites based on factors such as the historical performance of the pump at different sites, the time elapsed since the last use of each site, and the patient's personal preferences. The rotation feature could help to prevent overuse of certain sites, which can lead to tissue damage and decrease the effectiveness of the infusion. The site selection and mapping feature could also provide valuable data for healthcare professionals. For instance, it could generate reports that summarize the patient's infusion site habits and their impact on the therapy's performance. The reports could include visualizations, such as graphs or heat maps, that highlight patterns and trends in the data. This information could assist healthcare professionals in making informed decisions about the patient's therapy, such as whether to adjust the insulin dosage or recommend a different infusion site or hardware.

In addition, the site selection and mapping feature could be adapted for use in other disease areas that involve infusion therapy, such as chemotherapy for cancer treatment or intravenous nutrition for patients who are unable to eat or drink. In these cases, the feature could help to optimize the infusion process by identifying the most effective sites and tracking their performance over time.

In an embodiment intended for in-patient or professional care scenarios, the site mapping feature could be designed to manage multiple patients simultaneously. It could provide an overview of all the patients under a caretaker's supervision, showing the selected infusion sites and performance data for each patient. This could help caretakers to monitor their patients more efficiently and identify any issues that may require attention. The site mapping application/feature could also have integrated reminder functions to alert patients or caregivers about site change schedules. Customization of these reminders could be based on patient-specific data, such as average site performance, skin sensitivity, or lifestyle habits. Finally, the system could include a feature that uses machine learning techniques to predict the optimal infusion sites based on the patient's historical data and other relevant factors. This predictive feature could provide personalized recommendations that improve over time as the system learns more about the patient's response to the therapy.

Pressure may also be used to potentially eliminate the need for patient interaction with their insulin pump outside of setup, maintenance, and general use. For example, a system as disclosed herein may consider current sensing elements both native to the insulin pump system and the therapy (CGM, Pump) and new data streams both existing to the pump, partnering technologies (CGM), and external devices. External devices may include but are not limited to a heart rhythm monitor, heart rate monitor, SPO2 monitor, or smartphone. The system may accurately detect and characterize external events such as exercise, sleep, or eating and automatically adjust the infusion requirements based on the activity. This control system would be able to do this by estimating the insulin need based on the activity and deliver the correct amount accounting for any disturbances or infusion site/infusion set failures. Alternatively, the system can detect these events by assessing the insulin requirement based on blood glucose level, whether or not a site/set has failed, and if the blood glucose level is elevated with no signs of failure, the system can predict that user is eating and estimate the caloric density of the meal based on the rise in blood glucose. If no infusion failure event is present, then the system can assume any significant rise in blood glucose is based on an increased insulin need.

The previous detailed description has been provided for the purposes of illustration and description. Thus, although there have been described particular embodiments of a new and useful invention, it is not intended that such references be construed as limitations upon the scope of this invention except as set forth in the following claims.

What is claimed is:

1. A method for monitoring characteristics of a fluid being delivered from a fluid medication delivery device to an infusion site associated with a user, the method comprising:

a model creation and development stage comprising, for each of one or more associated fluid delivery operations:

collecting one or more time series data streams from one or more sensors corresponding to the fluid delivery operation;

assigning a fluid delivery state to the fluid delivery operation, and determining one or more fluid delivery characteristics of the fluid delivery operation based at least in part on one or more waveforms representing at least one of the collected one or more time series data streams; and generating one or more retrievable models correlating the one or more determined fluid delivery characteristics with the assigned fluid delivery state;

a model implementation stage for fluid delivery analysis with respect to a current subject, comprising:

collecting one or more time series data streams from one or more sensors corresponding to a fluid delivery operation with respect to the current subject;

identifying at least one of the models based on a selected fluid delivery state and one or more determined fluid delivery characteristics from the time series data streams corresponding to the current subject fluid delivery operation; and determining at least one correction factor to account for a difference between at least one observed fluid delivery value and a corresponding predicted fluid delivery value using the identified at least one model;

wherein the method further comprises generating one or more output signals based on the determined at least one correction factor.

2. The method of claim 1, wherein the collecting of one or more time series data streams in the model creation and development stage and the collecting of one or more time series data streams in the model implementation stage each comprise collecting the one or more time series data streams during a fluid delivery operation and further for a period of time after completion or suspension of the fluid delivery operation.

3. The method of claim 2, wherein the period of time is determined based at least in part on a target fluid delivery value and a rate of fluid delivery.

4. The method of claim 2, wherein the one or more determined fluid delivery characteristics are based at least in part on an observed subject response to the fluid delivery operation after completion or suspension of the fluid delivery operation.

5. The method of claim 1, further comprising, in association with the collecting of one or more time series data streams for each of the model creation and development stage and the model implementation stage, obtaining image data corresponding to at least an infusion site associated with the fluid delivery operation.

6. The method of claim 1, further comprising obtaining image data corresponding to at least an infusion site associated with the fluid delivery operation for a period of time after completion or suspension of the fluid delivery operation.

7. The method of claim 6, further comprising, in association with the collecting of one or more time series data streams for each of the model creation and development stage and the model implementation stage, obtaining image data corresponding to at least the infusion site during the fluid delivery, and wherein a two-dimensional image data collection during the fluid delivery operation transitions to a three-dimensional image data collection after the completion or suspension of the fluid delivery operation.

8. The method of claim 1, wherein the generated one or more output signals comprise control signals to at least one fluid delivery actuator.

9. The method of claim 1, wherein the generated one or more output signals comprise at least one signal to selectively trigger an alarm.

10. The method of claim 1, further comprising dynamically increasing a sampling rate for at least one of the one or more time series data streams for determining at least one of the one or more fluid delivery characteristics during the fluid delivery operation.

11. The method of claim 1, wherein the at least one correction factor is determined to account for a difference between an estimated and/or predicted amount of fluid delivered and an intended amount of fluid received.

12. The method of claim 11, further comprising predicting a wear time for an infusion set associated with the fluid delivery operation based at least in part on the at least one correction factor.

13. The method of claim 1, wherein the at least one correction factor is determined to account for a difference between a determined effect of the fluid delivery and a predicted effect of the fluid delivery.

14. The method of claim 11, wherein a cause of the difference between the amount of fluid delivered and the amount of fluid received is determined as relating to an infusion site, the method further comprising selectively determining an alternative infusion site for the fluid delivery operation when the infusion site is determined as relating to the difference between the amount of fluid delivered and the amount of fluid received.

15. The method of claim 13, wherein a cause of the difference between the determined effect of the fluid delivery and the predicted effect of the fluid delivery is determined as relating to at least one activity of the subject, and wherein the one or more output signals comprise at least one signal to trigger an alert relating to the at least one activity.

16. The method of claim 13, further comprising predicting a wear time for an infusion set associated with the fluid delivery operation based at least in part on the at least one correction factor.

17. The method of claim 1, wherein the correction factor is based at least in part on predicted values for one or more variables for which measured time series data streams are unavailable.

18. A system for monitoring characteristics of a fluid being delivered from a fluid medication delivery device to an infusion site associated with a user, the system comprising:

one or more processors communicatively linked to one or more sensors, and configured to direct the performance of:

a model creation and development stage comprising, for each of one or more associated fluid delivery operations:

collecting one or more time series data streams from one or more sensors corresponding to the fluid delivery operation;

assigning a fluid delivery state to the fluid delivery operation, and determining one or more fluid delivery characteristics of the fluid delivery operation based at least in part on one or more waveforms representing at least one of the collected one or more time series data streams; and generating one or more retrievable models correlating the one or more determined fluid delivery characteristics with the assigned fluid delivery state;

a model implementation stage for fluid delivery analysis with respect to a current subject, comprising:

collecting one or more time series data streams from one or more sensors corresponding to a fluid delivery operation with respect to the current subject;

identifying at least one of the models based on a selected fluid delivery state and one or more determined fluid delivery characteristics from the time series data streams corresponding to the current subject fluid delivery operation; and determining at least one correction factor to account for a difference between at least one observed fluid delivery value and a corresponding predicted fluid delivery value using the identified at least one model; and generating one or more output signals based on the determined at least one correction factor.

19. The system of claim 18, wherein the collecting of one or more time series data streams in the model creation and development stage and the collecting of one or more time series data streams in the model implementation stage each comprise collecting the one or more time series data streams during a fluid delivery operation and further for a period of time after completion or suspension of the fluid delivery operation.

20. The system of claim 18, further comprising, in association with the collecting of one or more time series data streams for each of the model creation and development stage and the model implementation stage, obtaining image data corresponding to at least an infusion site associated with the fluid delivery operation, during the fluid delivery operation and for a period of time after completion or suspension of the fluid delivery operation, wherein a two-dimensional image data collection during the fluid delivery operation transitions to a three-dimensional image data collection after the completion or suspension of the fluid delivery operation.

* * * * *